(12) United States Patent
Schumacher

(10) Patent No.: US 9,123,093 B1
(45) Date of Patent: Sep. 1, 2015

(54) VISION INSPECTION PROGRAMMING METHOD AND APPARATUS

(75) Inventor: David Schumacher, Franklin, WI (US)

(73) Assignee: Cognex Corporation, Natick, MA (US)

(*) Notice: Subject to any disclaimer, the term of this patent is extended or adjusted under 35 U.S.C. 154(b) by 1286 days.

(21) Appl. No.: 12/200,998

(22) Filed: Aug. 29, 2008

(51) Int. Cl.
*G06T 7/00* (2006.01)
*G06F 3/0481* (2013.01)

(52) U.S. Cl.
CPC ............ *G06T 7/0004* (2013.01); *G06F 3/0481* (2013.01)

(58) Field of Classification Search
CPC .............. G06T 7/0004; G06T 7/30108; G06T 2200/24; G05B 19/0426; G06K 9/6253; G06Q 10/06
USPC .......................................... 715/764, 777, 780
See application file for complete search history.

(56) References Cited

U.S. PATENT DOCUMENTS

| | | | |
|---|---|---|---|
| 4,674,043 A | 6/1987 | Hernandez et al. | |
| 5,481,712 A | 1/1996 | Silver et al. | |
| 5,721,847 A | 2/1998 | Johnson | |
| 5,742,504 A | 4/1998 | Meyer et al. | |
| 5,752,253 A | 5/1998 | Geymond et al. | |
| 5,768,158 A | 6/1998 | Adler et al. | |
| 5,933,638 A | 8/1999 | Cencik | |
| 6,115,042 A * | 9/2000 | Li et al. ........................ | 715/764 |
| 6,141,009 A | 10/2000 | Li et al. | |
| 6,282,699 B1 | 8/2001 | Zhang et al. | |
| 6,298,474 B1 * | 10/2001 | Blowers et al. ............... | 717/104 |
| 6,408,429 B1 | 6/2002 | Marrion, Jr. et al. | |
| 6,490,600 B1 | 12/2002 | McGarry | |
| 6,631,497 B1 | 10/2003 | Jamshidi et al. | |
| 6,701,513 B1 | 3/2004 | Bailey | |
| 6,763,515 B1 * | 7/2004 | Vazquez et al. ............... | 717/109 |
| 6,792,595 B1 | 9/2004 | Storistenau et al. | |
| 6,859,907 B1 * | 2/2005 | McGarry ...................... | 715/201 |
| 6,944,584 B1 * | 9/2005 | Tenney et al. .................. | 703/22 |
| 7,010,779 B2 | 3/2006 | Rubin et al. | |
| 7,051,317 B2 * | 5/2006 | Vazquez et al. ............... | 717/104 |
| 7,069,499 B1 | 6/2006 | McGarry | |
| 7,076,332 B2 | 7/2006 | Cifra et al. | |
| 7,079,141 B2 * | 7/2006 | Vazquez et al. ............... | 345/440 |
| 7,107,519 B1 * | 9/2006 | Webster et al. ............... | 715/212 |
| 7,139,979 B2 * | 11/2006 | Schultz et al. ................. | 715/763 |

(Continued)

OTHER PUBLICATIONS

InSight Vision Sensors—Product Guide Cognex (2003).*

Primary Examiner — Omar Abdul-Ali
Assistant Examiner — Phoebe Pan
(74) Attorney, Agent, or Firm — Quarles & Brady LLP

(57) ABSTRACT

A method and programming system for specifying vision inspection tools for a vision inspection system, the programming system comprising a workstation including a processor programmed to provide a first interface including a first view of a vision inspection system as the inspection system is being specified, the first interface usable to select vision inspection tools to be used in the vision inspection system from a first tool subset and a second interface including a second view of the vision inspection system as the inspection system is being specified, the second interface usable to specify vision inspection tools to be used with the vision inspection system from a second tool subset, the second interface also usable to specify script expressions that cannot be specified using the first interface, wherein, a developer can switch from the second interface to the first interface to observe the second view and the first view of the vision inspection system, respectively, during the inspection system specifying process.

34 Claims, 23 Drawing Sheets

(56) References Cited

U.S. PATENT DOCUMENTS

| | | | |
|---|---|---|---|
| 7,213,478 B2 * | 5/2007 | Harada et al. | 73/865.9 |
| 7,627,162 B2 * | 12/2009 | Blanford et al. | 382/141 |
| 7,769,222 B2 * | 8/2010 | Blanford et al. | 382/141 |
| 7,864,178 B2 * | 1/2011 | Marini et al. | 345/440 |
| 7,913,190 B2 * | 3/2011 | Grimaud et al. | 715/848 |
| 7,921,405 B2 * | 4/2011 | Gupta et al. | 717/102 |
| 7,975,213 B2 * | 7/2011 | Alden et al. | 715/219 |
| 7,984,371 B2 * | 7/2011 | Zdenek | 715/212 |
| 8,127,247 B2 * | 2/2012 | Tremblay et al. | 715/788 |
| 2002/0078086 A1 | 6/2002 | Alden et al. | |
| 2002/0186245 A1 * | 12/2002 | Chandhoke et al. | 345/764 |
| 2003/0036866 A1 * | 2/2003 | Nair et al. | 702/81 |
| 2003/0038841 A1 * | 2/2003 | Vazquez et al. | 345/762 |
| 2003/0038842 A1 * | 2/2003 | Peck et al. | 345/763 |
| 2003/0043175 A1 * | 3/2003 | Vazquez et al. | 345/700 |
| 2003/0120714 A1 * | 6/2003 | Wolff et al. | 709/200 |
| 2003/0227483 A1 * | 12/2003 | Schultz et al. | 345/763 |
| 2005/0171748 A1 * | 8/2005 | Oke | 703/6 |
| 2005/0283758 A1 | 12/2005 | Cobcroft et al. | |
| 2006/0005160 A1 | 1/2006 | Schultz et al. | |
| 2006/0107211 A1 * | 5/2006 | Mirtich et al. | 715/700 |
| 2006/0107223 A1 * | 5/2006 | Mirtich et al. | 715/764 |
| 2006/0123378 A1 * | 6/2006 | Cizl et al. | 716/18 |
| 2006/0150149 A1 | 7/2006 | Chandhoke et al. | |
| 2006/0171580 A1 * | 8/2006 | Blanford et al. | 382/141 |
| 2007/0014467 A1 * | 1/2007 | Bryll | 382/152 |
| 2007/0146491 A1 * | 6/2007 | Tremblay et al. | 348/211.99 |
| 2008/0025616 A1 * | 1/2008 | Bryll | 382/209 |
| 2008/0036873 A1 * | 2/2008 | Silver | 348/222.1 |
| 2008/0097621 A1 * | 4/2008 | Tasker et al. | 700/1 |
| 2008/0320408 A1 * | 12/2008 | Dziezanowski | 715/771 |
| 2009/0171719 A1 * | 7/2009 | Connington | 705/7 |

\* cited by examiner

Fig. 12

VISION INSPECTION PROGRAMMING METHOD AND APPARATUS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The present invention relates to vision systems and more specifically to a system and method for developing vision inspection programs for use by vision inspections systems. The resulting programs, when deployed, can be used to inspect parts and/or provide position information for guiding automated manipulations of such parts and/or machinery with respect to such parts.

Machine vision systems play an important role in automated systems. Cameras are used to obtain images of articles, and image processing is performed to identify features of the articles. Further image processing may be performed to identify an article's position, measure the article's dimensions, and/or to check for article defects. Image processing results may then be used to aid in the control of automated system components such as factory equipment, including, for example, an industrial controller, a robotic arm or a positioning table. Such machine vision systems may aid in the inspection, assembly, and/or handling of various types of articles, parts, and devices, including automotive parts (e.g., fuses, gaskets, and spark plugs), electrical components (e.g., connector pins, keyboards, LED, LCD, VFD displays), medical and pharmaceutical products (e.g., disposable test kits, syringes, needles, and date-lot codes), and consumer products (e.g., razor blades and floppy disks).

Whenever a new article, part, or device is inspected by a machine vision system, the vision processing component of the machine vision system will usually be modified to provide a new inspection program for the new item. For example, a system for automatically assembling (mounting) surface-mounted devices (SMDs) may run a vision inspection program for determining various characteristics (e.g., dimensions between edges, hole diameters, relative orientation to a surface to which the SMD is to be mounted, etc.) of each SMD as part of the mounting process. A different vision inspection program may be required to determine if a part that forms the surface to which an SMD is to be mounted is present, the part's orientation, part characteristics, etc. Where a first vision inspection program is used with a first SMD having a first characteristic set and a second vision inspection program is used with a second SMD having a second characteristic set, the first and second visions inspection programs may be different to identify the first and second different characteristic sets, respectively. Thus, for each new application that is not identical to an old application, a new inspection program typically has to be developed.

To enable custom vision inspection program design, sophisticated vision system manufacturers/providers typically bundle vision inspection program specifying software with system hardware where the software is used by a vision inspection developer (e.g., a customer) to select vision inspection system features, options or tools, to set inspection system variables and values, to select image features to be analyzed, to formulate useful vision inspection functions and expressions, etc. Here, the bundled software often includes a huge number (e.g., one hundred) of software based vision inspection tools that can be selected and for which variables can be set to build virtually an endless number of custom vision inspection programs to meet requirements of literally an endless list of applications. The software based inspection tools are typically specifiable via an interface presented on a computer display screen.

One interface for defining machine vision inspection programs is referred to generally as a scripting or programming interface. A scripting interface is one where an inspection system developer actually enters lines of program instructions that, when run by an inspection system, cause the system to perform a desired inspection process. In general a scripting interface is referred to as a full featured interface because the interface enables a user to specify or develop all inspection system features that are supported by the inspection system. While scripting interfaces have been useful in many applications, such interfaces are particularly difficult to use and require highly skilled developers trained in various programming languages.

One other useful inspection system specifying interface is referred to as a spreadsheet interface. U.S. Pat. No. 7,107,519 which issued on Sep. 12, 2006 and which is titled "Spread-Sheet Based User Interface Creation" and which is assigned to Cognex Corporation, describes an exemplary spreadsheet interface for programming vision inspection systems. Similarly, U.S. patent application Ser. No. 09/635,365 filed "Machine Vision Sensor" which was filed on Aug. 9, 2000 teaches various aspects of a spreadsheet interface. Both the patent and application referenced here are incorporated by reference in their entirety. As the label implies, the spreadsheet interface presents a spreadsheet image via a display screen that includes rows and columns of cells. Cell content is specified by a developer during an options specifying process and may include functions, mathematical expressions, data labels, or data to be processed according to an inspection program. In addition input and/or output functions can be placed in cells where input functions read information from hardware devices and output functions interact with specialized hardware devices. Together, the cell expressions in a spreadsheet define the inspection program. The spreadsheet interface, like the scripting interface, is a full featured interface because it can be used to specify or develop all inspection system features that are supported by the inspection system.

In at least some known spreadsheet interface systems, an inspection program developer can select predefined inspection objects or tools from a list of possible tools to be added to an inspection program. Here, each tool is often associated with a multi-step function set that is performed during an inspection process. When an inspection tool is selected, a set of spreadsheet cells is filled in with functions, expressions, labels and data that together define the inspection tool process. In some cases a dialog box opens up where a selected tool requires the developer to specify some value or values, input(s) or output(s).

In addition to placing functions and expressions in cells when predefined inspection tools are selected, a developer can develop custom tools, expressions and the like in any cell where other cells are referenced. Thus, a developer can use the spread sheet to develop custom inspection tools.

While the spreadsheet view is useful to develop inspection programs, spreadsheet views are not completely intuitive and the cell functions, expressions and data have a complicated format and a relatively messy appearance such that it takes some time to become proficient at programming with a spreadsheet interface and the end product is somewhat intimidating to view and work with during and after the programming process.

Yet one other type of particularly useful interface is generally referred to as a point-and-click (P&C) interface. As the label implies, a P&C interface allows a developer to select inspection options, set operating parameters, etc., using a point-and-click input device such as a mouse that controls an on screen cursor or the like. Here, the software can operate to guide a developer along the process of developing an inspection program. When some point-and-click options are selected, parameter fields or boxes may be opened to allow a developer to specify or selecting various inspection tool operating parameters. As inspection tools and operating parameters are selected and specified, the selections are used behind the scenes by a compiler to generate scripted programming code, functions and expressions which define the overall system inspection program.

One problem with some inspection programming systems is that the number of inspection tools supported by the systems and that the systems are capable of supporting can be huge (e.g., hundreds) such that, if presented in their entirety, the tool options could cause confusion for developers and could exacerbate the task of becoming a proficient inspection program developer.

Here, it has been recognized that, while a complete system may include several hundred inspection tools to choose from and may be able to support a virtually endless number of different inspection tools, (1) a relatively small subset of available/possible inspection tools are typically common among most (e.g., a large percentage of) vision inspection programs and (2) that the small subset of common inspection tools often represent a large percentage of inspection tools needed to instantiate any given inspection program. Thus, for instance, assume that an inspection specifying program supports 200 possible inspection tools and could support a virtually endless set of inspection tools (i.e., if the tools were specified). Also assume that two different programs are developed to inspect two different parts. Here, where the first inspection program for a first part includes fifteen different tools (and may include multiple instances of each of the fifteen different tools), it is very likely that the second inspection program will include a large number of the 15 tools (e.g., 13-14) included in the first program. Where the second program includes a total of 15 tools and 13 of the 15 tools are common with the first program, both the first and second programs could be developed using an inspection specifying program that includes only 17 inspection tools (i.e., the 15 tools for the first program and the additional 2 uncommon tools required to develop the second program) instead of a program including all 200 inspection options or a program offering an endless number of inspection tool options.

Similarly, where 20 different inspection programs are to be developed, it may be that all 20 programs could be developed using an inspection specifying program that includes only 25 different inspection tools instead of a program including 200 or more tools. Thus, by providing a point-and-click type specifying tool that includes a subset of available/possible tools, developer confusion is minimized and ease of use is increased appreciably.

As another refinement, inspection specifying programs can be developed for specific industries where the subset of possible inspection options that is made available to developers is specifically tailored to the specific industry. For instance, industries that need to determine liquid levels in clear containers may be provided with a different subset of available inspection options than industries that need to measure dimensions between parallel edges. In this case, in the liquid level measuring industry 10 inspection options may be usable to define 99% of all inspection programs while 40 options are required in the dimension measuring industry to define 99% of all programs.

While P&C interfaces that present only a subset of available inspection tools work well in some cases, at times a developer will desire or need inspection tools that, while available or at least possible using the full suite of development tools, are not presented via the P&C interface because of decisions made by the interface designer. Thus, for instance, in a case where 25 inspection options are presented to a developer via a point-and-click type interface, at times the developer may want to use eight other available or possible options in specific applications.

Here one solution has been to provide a programming interface that includes both point-and-click and scripting/programming capabilities where a P&C interface presents a subset of available inspection tools and a scripting interface can be used to specify the balance of required inspection tools. Here, when the point-and-click interface is accessed, the point-and-click interface operates as a front end to the scripting interface so that, as inspection tools are selected using the point-and-click interface, program segments are filled in with functions, expressions and data consistent with the point-and-click interface selections. When a developer needs a tool that is not presented by the point-and-click interface, the developer switches views to the scripting view and specifies other tools or defines other required functions.

While dual P&C and scripting interface systems can be used to successfully program vision processes, currently known dual interface systems have several important shortcomings. First, in known dual P&C/scripting interface systems, after a user moves from the P&C view to the scripting view and adds a new vision processing tool or changes a tool parameter using the scripting view, if the user moves back to the P&C view, there is no representation of the new vision processing tool or changed parameter in the P&C view. Inability to see P&C representations of scripted tools can generally cause confusion for inexperienced developers during an inspection system specifying process.

Second, known systems do not have a way for a developer to create new P&C interface tools that the developer would like to use routinely during subsequent development activities. For instance, a developer may routinely want to employ an inspection tool that performs a sequence of fifteen inspection functions to yield one or more useful results and that tool may not be selectable via the P&C interface so that, each time the developer wants to use the tool, the developer has to go to the scripting interface and recreate the fifteen function sequence. Clearly the inability to specify the fifteen function sequence once and represent that function for selection via the P&C interface thereafter exacerbates the task of developing inspection systems considerably.

Third, developers cannot change existing P&C tools to hide existing properties, change behaviors of existing tools, change default properties and/or behaviors of P&C tools such that all future instances will use the new defaults or tie behaviors of two or more tool instances together. These short comings mean that tool customization has to be done using scripting alone and result in a system where routine customization has to be performed repetitively which exacerbates the development process.

Thus, it would be advantageous to have an inspection program specifying system that allows a developer to move freely between scripting and P&C interfaces where at least some scripted customization is represented in the P&C interface and where P&C tool modification and new P&C tools specified in script can be saved to persist for use thereafter.

BRIEF SUMMARY OF THE INVENTION

It has been recognized that a dual interface vision inspection specifying system can be configured wherein a developer can switch freely back and forth in a round trip fashion between the two interfaces and wherein the interfaces can be provided with features that are particularly suitable for simply and intuitively performing different types of programming or specifying processes. It has also been recognized that, while the two interfaces are separate and distinct, changes made using one of the interfaces can be reflected in the other of the two interfaces. Thus, for instance, a first or point-and-click interface may enable a developer to intuitively select various tools and tool property values required to construct an inspection system while a second programming or scripting type interface may be useable to, in addition to selecting tools and setting property values, specify new or additional tools, change (i.e., add, delete or modify) properties of existing tools, hide or expose properties of an instance of a P&C tool, change the behavior of an instance of a P&C tool, modify existing tool property values, and so on. Here, after a new tool has been specified or an existing tool has been altered using the programming or scripting interface, in at least some embodiments changes to the tool set, tool properties, default properties/behaviors, etc., may automatically be represented in the point-and-click interface while in other cases a developer may be able to specify that the changes should be represented in the point-and-click interface. In addition, new or modified tools can be stored as tool templates for subsequent use in a current or future inspection system specifying process.

Consistent with the above, some embodiments of the present invention include a programming system for specifying vision inspection tools for a vision inspection system, the programming system comprising, a processor, a display screen for presenting interfaces to a developer, an input device for receiving information from the developer, the received information specifying a vision inspection system, wherein the processor is programmed to provide: (i) a first interface including a first view of a vision inspection system as the inspection system is being specified, the first interface usable to at least one of select vision inspection tools to be used in the vision inspection system from a first tool subset and to set tool properties in a first properties subset for each of a plurality of vision inspection tools and (ii) a second interface including a second view of the vision inspection system as the inspection system is being specified, the second interface usable to specify at least one of vision inspection tools to be used with the vision inspection system from a second tool subset and to set tool properties in a second properties subset for each of the tools in the second tool subset, the second interface also usable to specify script expressions that cannot be specified using the first interface, wherein, a developer can switch from the second interface to the first interface to observe the second view and the first view of the vision inspection system, respectively, during the inspection system specifying process and, wherein, at least a subset of changes made to the vision inspection system using the second interface are represented as changes to the first interface.

In some cases the first interface is usable both specify vision inspection tools to be used with the vision inspection system from the first tool subset and to set tool properties in the first properties subset for each of the tools in the first tool subset. In some cases the first tool subset includes a subset of the tools in the second tool subset. In some cases the second tool subset includes all of the tools available for specifying a vision inspection system. In some cases the first interface is a point-and-click interface. In some cases the second interface includes a spreadsheet interface wherein inspection program expressions and values corresponding to inspection tools are presented in cells of the spreadsheet interface.

In some cases the spreadsheet interface specifies cell set templates for at least a subset of the inspection tools where, when one of the inspection tools is selected using either one of the first interface and the second interface, an instance of the cell set template associated with the selected inspection tool is added to the spreadsheet view. In some cases at least a subset of the cell set templates include properties that may be accessed via the first interface and wherein the second interface can be used to render the properties accessible or inaccessible via the first interface. In some cases the second interface can be used to modify at least one of the first tool subset, the first properties subsets for tools in the first tool subset and values associated with the first properties for tools in the first tool subset.

In some cases the second interface can be used to modify each of the first tool subset and each of the first properties subsets for the tools in the first tool subset. In some cases the second interface can be used to modify the first tool subset by at least one of adding a tool to the first tool subset and deleting a tool from the first tool subset. In some cases the second interface can be used to expose and hide properties of an instance of a tool on the first interface. In some cases the second interface can be used to modify an existing tool and to store a new cell set template including cells that reflect changes to the existing tool where the new cell set template can be used subsequently to instantiate another instance of a tool having properties consistent with the new cell set template. In some cases the second interface can be used to create a new vision inspection tool and to store a new cell set template including cells that specify the new tool, the second interface also usable to render the new tool accessible via the first interface. In some cases a first set of changes to a vision inspection system made using the second interface are represented in the first interface and a second set of changes to the vision inspection system made using the second interface do not alter the first interface. In some cases each change made to the vision inspection system using the first interface is represented in the second interface.

Other embodiment include a programming system for specifying vision inspection tools for a vision inspection system, the programming system comprising a processor, a display screen for presenting interfaces to a developer, an input device for receiving information the developer, the received information specifying a vision inspection system, the processor is programmed to provide (i) a first interface including a first view of a vision inspection system as the inspection system is being specified, the first interface usable to select vision inspection tools to be used in the vision inspection system from a first tool subset and to set tool properties in a first properties subset for each of the tools in the first tool subset and (ii) a second interface including a second view of the vision inspection system as the inspection system is being specified, the second interface usable to specify vision inspection tools to be used with the vision inspection system from a second tool subset and to set tool properties in a second properties subset for each of the tools in the second tool subset, the second interface also usable to specify script expressions that cannot be specified using the first interface, wherein, a developer can switch back and forth between the first interface and the second interface to observe the first view and the second view of the vision inspection system, respectively, during the inspection system specifying process and wherein, the developer can use the second interface view to change the first tool subset and the first properties subsets thereby changing the tools selectable and the properties settable via the first interface, respectively.

In some cases the first interface is a point-and-click interface. In some cases the second interface includes a spreadsheet interface wherein inspection program expressions and values corresponding to inspection tools are presented in cells of the spreadsheet interface. In some cases the spreadsheet interface specifies cell set templates for at least a subset of the inspection tools where, when one of the inspection tools is selected using either one of the second interface and the first interface, an instance of the cell set template associated with the selected inspection tool is added to the spreadsheet view.

In some cases at least a subset of the cell set templates include properties that may be accessed via the first interface and wherein the second interface can be used to render the properties exposed or hidden via the first interface. In some cases the second interface can be used to modify the first tool subset by at least one of adding a tool to the first tool subset and deleting a tool from the first tool subset. In some cases the second interface can be used to modify an existing tool and to store a new cell set template including cells that reflect changes to the existing tool where the new cell set template can be used subsequently to instantiate another tool instance having properties consistent with the modified existing tool. In some cases each change made to the vision inspection system using the first interface is reflected in the second view of the inspection system.

In some cases the first tool subset includes a subset of the tools in the second tool subset. In some cases the second tool subset includes all of the tools available for specifying a vision inspection system.

Still other embodiments include a method for specifying vision inspection tools for a vision inspection system, the method comprising the steps of providing a first interface including a first view of a vision inspection system as the inspection system is being specified, the first interface usable to at least one of select vision inspection tools to be used in the vision inspection system from a first tool subset and to set tool properties in a first properties subset for each of a plurality of vision inspection tools and providing a second interface including a second view of the vision inspection system as the inspection system is being specified, the second interface usable to specify at least one of vision inspection tools to be used with the vision inspection system from a second tool subset and to set tool properties in a second properties subset for each of a plurality of vision inspection tools, the second interface also usable to specify script expressions that cannot be specified using the first interface, allowing a developer to switch from the second interface to the first interface to observe the second view and the first view of the vision inspection system, respectively, during the inspection system specifying process and, wherein, at least a subset of changes made to the vision inspection system using the second interface are represented as changes to the first interface.

Yet other embodiments include a method for specifying vision inspection tools for a vision inspection system, the method comprising the steps of providing a first interface including a first view of a vision inspection system as the inspection system is being specified, the first interface usable to select vision inspection tools to be used in the vision inspection system from a first tool subset and to set tool properties in a first properties subset for each of the tools in the first tool subset and providing a second interface including a second view of the vision inspection system as the inspection system is being specified, the second interface usable to specify vision inspection tools to be used with the vision inspection system from a second tool subset and to set tool properties in a second properties subset for each of the tools in the second tool subset, the second interface also usable to specify script expressions that cannot be specified using the first interface and allowing a developer to switch back and forth between the first interface and the second interface to observe the first view and the second view of the vision inspection system, respectively, during the inspection system specifying process, wherein, the developer can use the second interface view to change the first tool subset and the first properties subsets thereby changing the tools selectable and the properties settable via the first interface, respectively.

Yet other embodiments include a programming system for specifying vision inspection tools for a vision inspection system, the programming system comprising a computer including a display screen and an input device, the screen for presenting interfaces to a developer and the input device for receiving developer input from the developer, a point-and-click specifying interface presentable via the display screen, the point-and-click specifying interface for selecting and defining at least a subset of vision inspection tools and a spreadsheet interface wherein inspection program expressions and values are presented in cells of the spreadsheet, the spreadsheet interface for selecting and defining a second subset of vision inspection tools, wherein, a developer can move between the point-and-click specifying interface and the spreadsheet interface to observe a point-and-click view and a spreadsheet view of the specified vision inspection tools, respectively, during a vision inspection specifying process.

In some cases at least a subset of the changes made using either one of the point-and-click interface and the spreadsheet interface are represented in changes to the other of the point-and-click interface and the spreadsheet interface. In some cases the spreadsheet interface is usable to specify script expressions that cannot be specified using the point-and-click interface.

Yet other embodiments include a method for specifying vision inspection tools for a vision inspection system, the method comprising the steps of providing a point-and-click specifying interface via a display screen, the point-and-click specifying interface for selecting and defining at least a subset of vision inspection tools, providing a program scripting interface for selecting and defining a second subset of vision inspection tools and receiving developer changes to a set of selected inspection tools where the changes are made using the program scripting interface and when a developer uses the program scripting interface to change a set of selected inspection tools, modifying the point-and-click interface to reflect the program scripting interface changes.

Some cases further include the steps of, after receiving developer changes to a set of selected inspection tools where the changes are made using the scripting interface, when the developer accesses the point-and-click interface, presenting the modified point-and-click interface. In some cases the scripting interface includes a spreadsheet interface wherein inspection program expressions and values are presented in cells of the spreadsheet interface.

In some cases developer changes using the scripting interface may expose or hide tool properties on the point-and-click interface, change behavior or properties of an instance of a tool selected via the point-and-click interface, change default properties or default behaviors of tools selectable via the point-and-click interface such that subsequently specified instances of the tools using the point-and-click interface will include the defaults, add a custom tool to the point-and-click interface and create a new point-and click interface tool.

Yet other embodiments include a method for specifying vision inspection tools for a vision inspection system, the method comprising the steps of providing a point-and-click specifying interface via a display screen, the point-and-click specifying interface for selecting and defining at least a subset of vision inspection tools and providing a spreadsheet interface via the display screen for selecting and defining a second subset of vision inspection tools and receiving developer changes to a set of selected inspection tools where the changes are made using the point-and-click specifying interface, when a developer uses the point-and-click specifying interface to change a set of selected inspection tools, modifying the spreadsheet interface to reflect the point-and-click specifying interface changes.

Some embodiments further include the steps of, after receiving developer changes to a set of selected inspection tools where the changes are made using the point-and-click specifying interface, receiving a command from the developer to access the spreadsheet interface and presenting the modified spreadsheet interface. In some cases a developer uses the spreadsheet interface to specify a portion of the vision inspection system, the portion specified via the spreadsheet interface is represented in the point-and-click interface.

Yet other embodiments include a programming system for specifying vision inspection tools for a vision inspection system, the programming system comprising a processor, a display screen for presenting interfaces to a developer, an input device for receiving information from the developer, the received information specifying a vision inspection system, wherein the processor is programmed to provide (i) a first interface including a first view of a vision inspection system as the inspection system is being specified, the first interface usable to select vision inspection tools to be used in the vision inspection system from a first tool subset and (ii) a second interface including a second view of the vision inspection system as the inspection system is being specified, the second interface also usable to select vision inspection tools to be used in the vision inspection system, the second interface further usable to alter the first tool subset by at least one of changing default properties of tools in the first tool subset, changing default behaviors of tools in the first tool subset, adding new tools to the first tool subset and deleting tools from the first tool subset.

In some cases the first and second interfaces are a point-and-click interface and a scripting interface, respectively. In some cases the scripting interface is a spreadsheet interface.

To the accomplishment of the foregoing and related ends, the invention, then, comprises the features hereinafter fully described. The following description and the annexed drawings set forth in detail certain illustrative aspects of the invention. However, these aspects are indicative of but a few of the various ways in which the principles of the invention can be employed. Other aspects, advantages and novel features of the invention will become apparent from the following detailed description of the invention when considered in conjunction with the drawings.

BRIEF DESCRIPTION OF THE SEVERAL VIEWS OF THE DRAWINGS

FIG. 12 is similar to FIG. 6, albeit showing the interface at a different time during the specifying process;

DETAILED DESCRIPTION OF THE INVENTION

Figure 1:
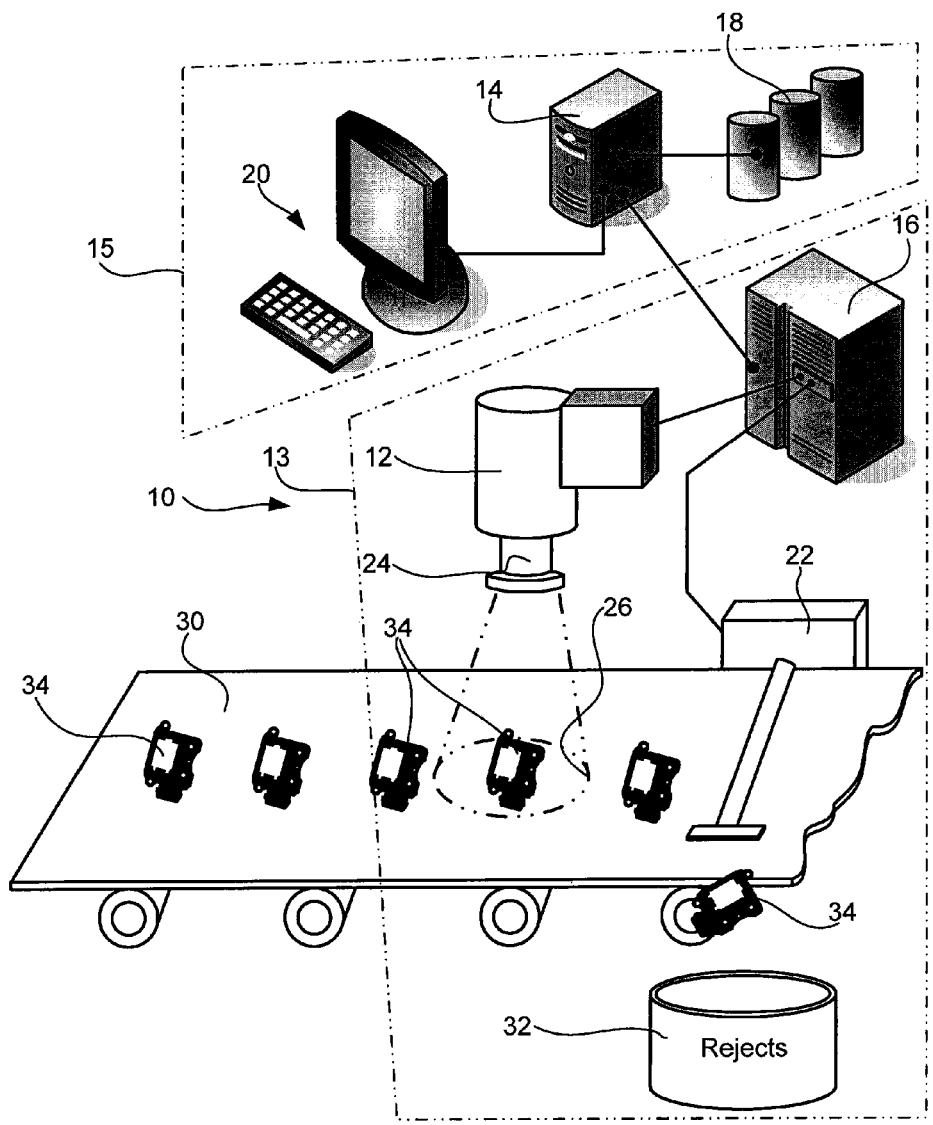
FIG. 1 is a schematic view illustrating an inspection system and an inspection process specifying subsystem consistent with at least some aspects of the present invention.

One or more specific embodiments of the present invention will be described below. It is specifically intended that the present invention not be limited to the embodiments and illustrations contained herein, but include modified forms of those embodiments including portions of the embodiments and combinations of elements of different embodiments as come within the scope of the following claims. It should be appreciated that in the development of any such actual implementation, as in any engineering or design project, numerous implementation-specific decisions must be made to achieve the developers' specific goals, such as compliance with system-related and business related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure. Nothing in this application is considered critical or essential to the present invention unless explicitly indicated as being "critical" or "essential."

Referring now to the drawings wherein like reference numerals correspond to similar elements throughout the several views and, more specifically, referring to FIG. 1, the present invention will be described in the context of an exemplary machine vision inspection system 10 for processing or otherwise acting upon articles of a similar type in a repeated and automated fashion. System 10 includes, among other components, a conveyor belt 30 supporting a plurality of articles 34, an inspection subsystem 13 and an inspection program specifying subsystem 15. Inspection subsystem 13 includes, among other components, a server 16 which runs article inspection processing software that is coupled to a camera 12 and a diverter component 22.

Camera 12 includes a lens 24 having a field of view 26 and obtains images of a scene which may include the area encompassing all pertinent portions of an article 34 in the field of view 26 and the area around article 34. The inspection process is performed on the image of the scene and the results are forwarded to a display for viewing. If the article passes an inspection process, article 34 is kept on the conveyor 30 for subsequent processing and/or handling. However, if an article inspection fails, the failed article may be removed from conveyor 30 by diverter 22 and deposited into a rejects bin 32.

Referring still to FIG. 1, the exemplary inspection program specifying subsystem 15 includes a workstation including a computer 14 (e.g., a processor), an electronic computer display screen 20, one or more input devices 21 (a keyboard shown) and one or more databases 18. Computer 14 is linked to server 16 to receive an exemplary commissioning image of one of the articles 34 during an inspection program specifying process. Using subsystem 15, a program developer selects several vision inspection tools, tool properties, and property values, thereby defining a machine vision process. Once the machine vision process has been completely specified, data representing the process is compiled to generate an inspection control program which is then downloaded from computer 14 to server 16 to control the machine vision process during normal operation.

Referring still to FIG. 1, during the inspection program specifying process, the operator is presented with inspection program specifying interfaces via display screen 20 and uses one or more input devices 21 to select the machine vision tools, specify properties and property values, to select various features in the commissioning image and select and specify other parameters required to completely define the inspection program.

Figure 2:
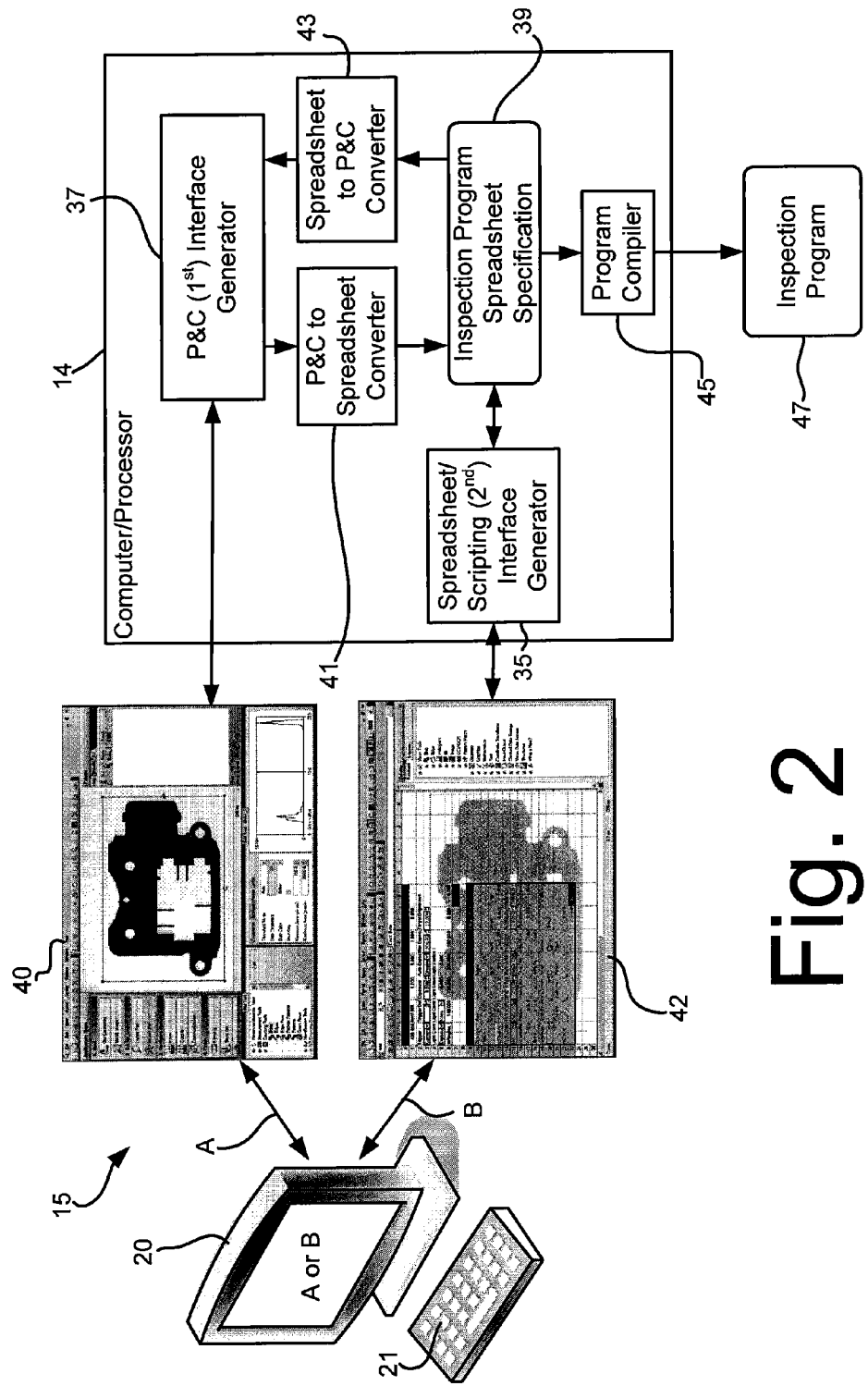
FIG. 2 is a schematic view illustrating the inspection process specifying system of FIG. 1 in more detail.

Referring now to FIG. 2, a more detailed view of the inspection program specifying subsystem 15 is shown. Computer 14 runs software programs stored in the databases 18 (see FIG. 1) to facilitate various functions during the inspection program specifying process. First, computer 14 facilitates a first interface generator function (see generator 37) to generate a point-and-click interface 40 via display screen 20 for providing on-screen inspection program specifying tools to a program developer and to receive specifying information from the developer via the interface. Second, computer 14 facilitates a spreadsheet/scripting or second interface generator function (see generator 35) to, as an alternate to the point-and-click interface 40, generate a spreadsheet or scripting interface 42 presented via display 20. Here, interface 42 provides various inspection program specifying tools usable by an operator to specify inspection program functions and processes.

Referring still to FIG. 2, as inspection program features and functions are specified using the spreadsheet/scripting interface 42, generator 35 forms an inspection program spreadsheet specification 39 which includes all of the information specified by the developer. In addition, as the developer uses the point-and-click interface 40 to specify inspection program features and functions, the point-and-click interface generator 37 provides the specified information to a point-and-click to spreadsheet converter 41 which, as the label implies, converts the specified information to a form suitable to fill in cells of the spreadsheet in the inspection program spreadsheet specification 39 so that, regardless of which interface, 40 or 42, is used to specify inspection program functions and features, the specified information is included in spreadsheet specification 39. Furthermore, computer 14 facilitates a spreadsheet to point-and-click converter function (see converter 43) which converts at least a subset of the spreadsheet specification information to a form that can be used by the point-and-click interface generator 37 to generate point-and-click interface 40 such that interface 40 is consistent with information stored in spreadsheet specification 39.

Referring still to FIG. 2, after one or both of the interfaces 40 and 42 have been used to fully specify a spreadsheet specification 39 that defines a complete inspection program, computer 14 operates as a program compiler 45 to compile the spreadsheet specification information and generate an inspection program 47. Referring once again to FIG. 1, after program 47 has been generated, the inspection program 47 is downloaded to server 16 which then runs the program during normal operation to inspect articles 34 and to, in the present example, control diverter 22 and conveyor 30 as appropriate.

Figure 3:
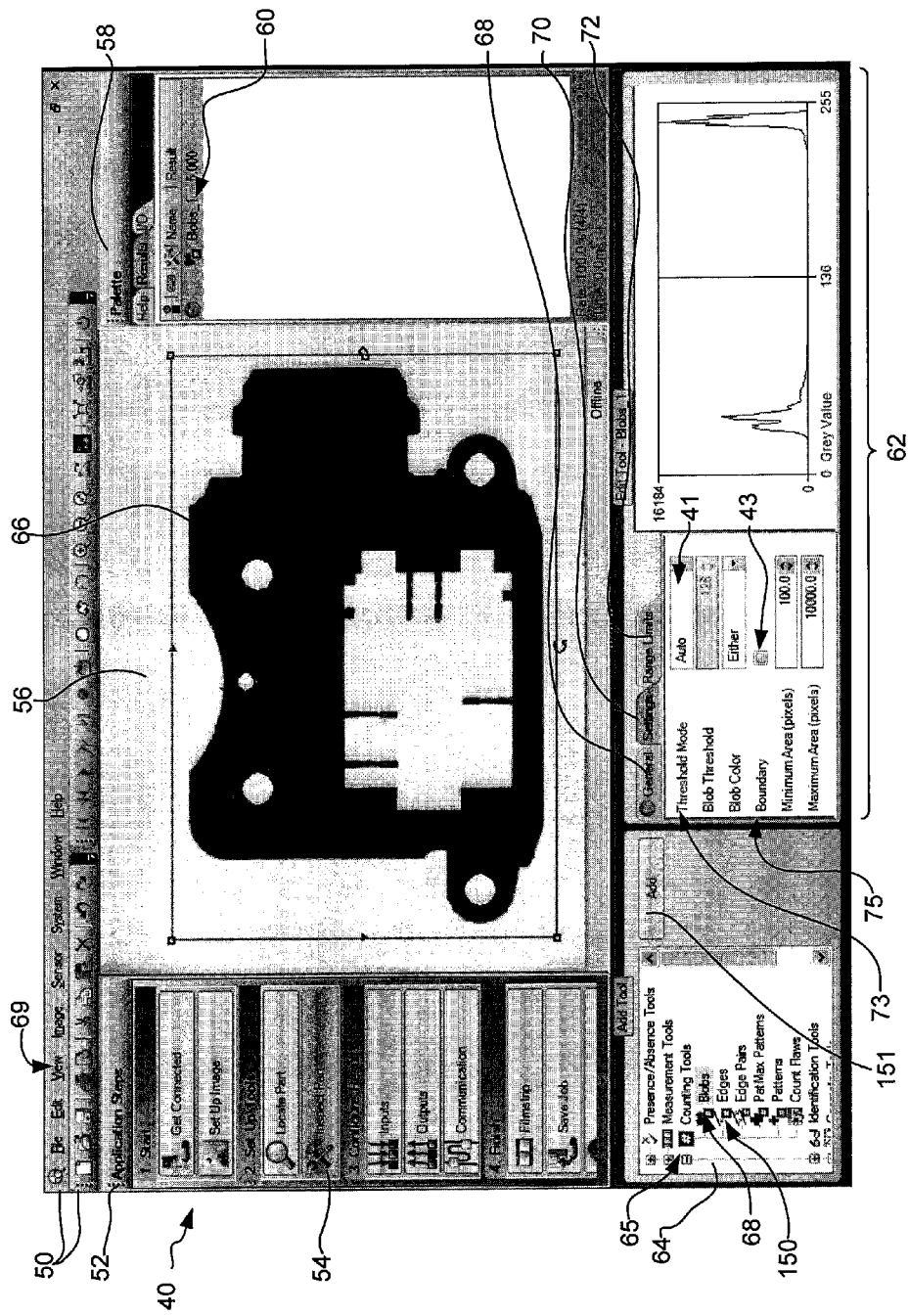
FIG. 3 is a screenshot illustrating an exemplary point-and-click type interface that is consistent with at least some aspects of the present invention.
Figure 4:
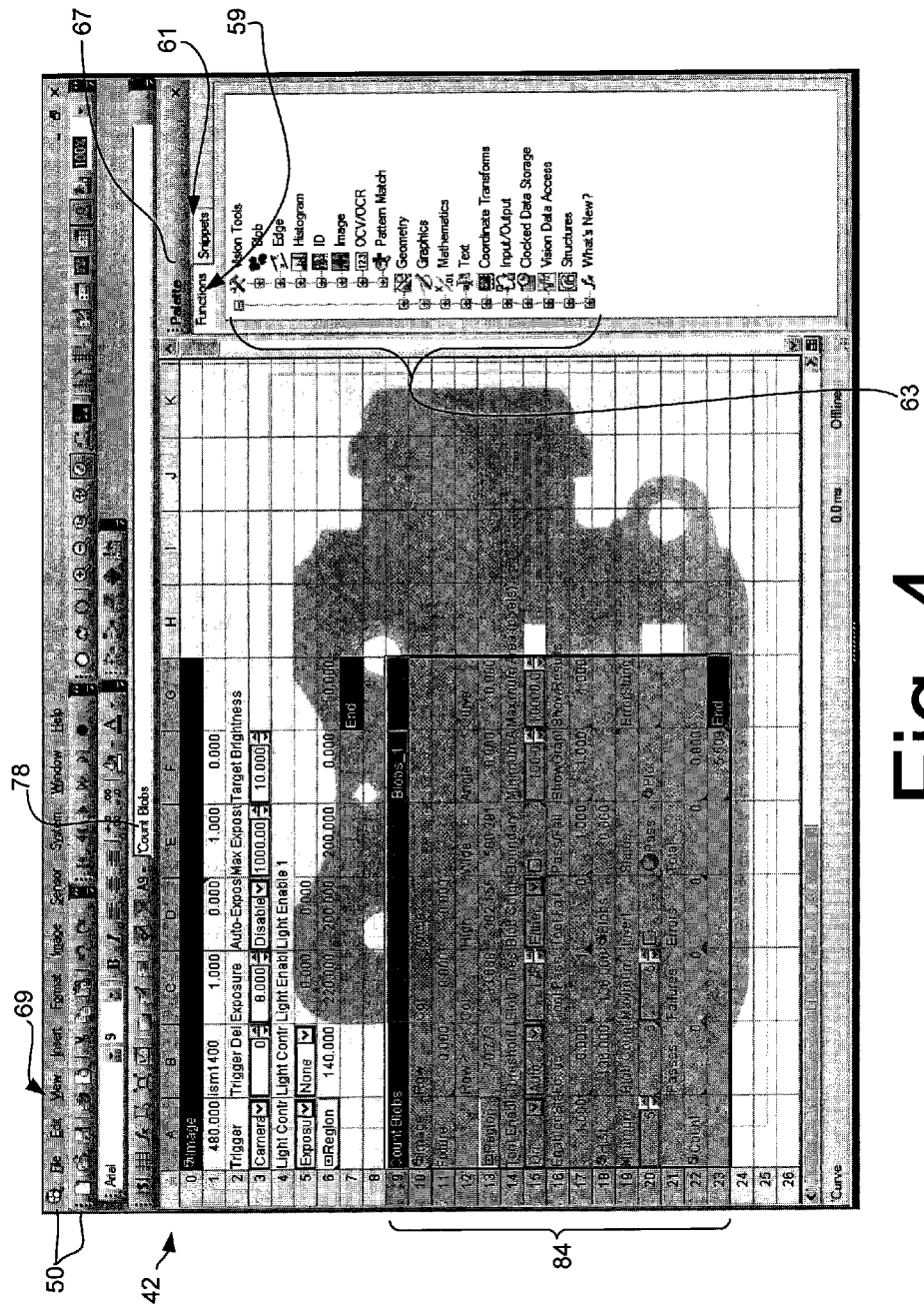
FIG. 4 is a screenshot illustrating an exemplary spreadsheet or scripting interface that is consistent with at least some aspects of the present invention.

Referring now to FIGS. 3 and 4, FIG. 3 includes a screen-shot of an exemplary first or point-and-click type interface 40 while FIG. 4 includes a screenshots of an exemplary spreadsheet type interface 42 that are consistent with at least one embodiment of the present invention. Hereafter, while FIGS. 3-22 each includes a screenshot, the screenshot will be referred to as interfaces to simplify this explanation. Referring specifically to FIG. 3, the point-and-click interface 40 includes an image space 56 generally centrally located with a plurality of tool bars surrounding the image space 56. Interface 40 presents or is useable to access a first tool subset and, for each tool in the first tool subset, a first properties subset where the tools and properties can be selected and/or set during an inspection system specifying process. To this end, the tool bars include two standard interface control toolbars 50 along a top edge of the interface 40, an application steps toolbar 52, an add tool menu 64, an edit tool space 62, and a palette space 58. The standard toolbars 50 along the top edge of interface 40 include typical Windows type tools that allow an operator to open a file, close a file, save a file, edit a file, change windows in a window-based system, receive help regarding various topics related to image control, and so on. One important feature provided by toolbars 50 is the change view option 69 that can be selected by a developer to switch between the point-and-click view shown in FIG. 3 and the spreadsheet/scripting view shown in FIG. 4. Thus, here, it should be appreciated that by selecting option 69, the developer opens a pull-down menu (not illustrated) that would include, among other options, a selection corresponding to the spreadsheet view when point-and-click interface 40 is currently shown, and, similarly, when the spreadsheet interface 42 in FIG. 4 is currently shown, the view pull-down menu would include a point-and-click option for switching back to interface 40.

Referring still to FIG. 3, application steps menu 52 includes a number of different onscreen buttons that can be selected by a developer to move through the inspection program specifying process. Among other buttons provided in the application steps menu 52, an inspect part button 54 is provided which, when selected, provides other tools via interface 40 that can be used by the developer to specify inspection program functions and features.

The add tool menu 64 provides a list of tools associated with a selected one of the buttons in the application steps menu 52 that can be used by a developer to specify program functions and features associated with a selected application steps button. In FIG. 3, selectable tools are shown in space 64 corresponding to the inspect part button 54 selected in the application steps menu 52. One general tool type shown in the add tool space 64 is referred to as counting tools 65 under which a number of different specific counting tools are listed, including blobs 68 and edges 150 for, as the label implies, counting Blobs and Edges, respectively, within an obtained image or a portion of an obtained image. The add tool menu also includes an "add" button 151 that is selectable to add an instance of one of the tools from menu 64 to an inspection program.

Referring to FIG. 3, palette space 58 lists separate instances of each of the tools that have been added to an inspection program. In FIG. 3, only a single instance of one tool, Blobs 1, identified by numeral 60, is shown. As other tools are added to the inspection program, the added tools are included in the palette list.

Referring yet again to FIG. 3, edit tool space 62 provides properties or parameters that are associated with a currently selected specific instance of a tool included in an inspection program and, in at least some cases, enables a developer to modify property or parameter values. In the exemplary interface 40, the tool instance "Blobs 1" is currently selected and therefore related properties and values are provided in the edit tool space 62. In at least some embodiments, as shown, the tool properties are grouped into three categories, including a general category, a settings category and a range limits category, which are separately selectable via tabs 68, 70 and 72, respectively. In FIG. 3, the settings tab 70 has been selected and therefore settings properties and related values are shown in space 62. Exemplary settings properties include a threshold mode property 73 and a boundary property 75 as well as a blob threshold property, a blob color property, a minimum area property and a maximum area property. Values and settable parameters 41 and 43 are associated with the threshold mode and boundary properties 73 and 75, respectively.

Referring still to FIG. 3, a commissioning image 66 of one of the articles 34 (see again FIG. 1) is provided in image space 56. During a program specifying process, when a developer selects "inspect part" button 54, inspection tools are provided in a directory format in menu 64. When blobs tool 68 is selected and then add button 151 is selected, the Blobs 1 instance 60 of the blobs tool is added to palette 58 and property values are provided in space 62 corresponding to the Blobs 1 instance. Here, the Blobs 1 label may be a default label assigned to the first instance of the Blobs counting tool and a developer may be able to modify the label. Default or initial property values are assigned to each of the Blobs 1 properties. In some cases the property value choices may be binary (e.g., auto or manual options for threshold mode 73) while in the other cases more options are available. In some cases a range of integer options may be provided (e.g., 1 to 1000 for a minimum pixel area) and a selection field and up/down arrows may be provided (see field associated with minimum area property in space 62) for the developer to use to select property values. Hereafter a field including up/down range selection arrows will be referred to as a range setting field. The developer can modify parameter values using the fields and other interface tools and buttons provided in space 62.

At some point, referring still to FIG. 3, the developer may decide to switch to the spreadsheet interface 42 shown in FIG. 4. To switch from interface 40 to interface 42, as explained above, the operator selects view option 69 from toolbar 50 which opens a pull-down menu and then selects the spreadsheet interface or spreadsheet view option from the pull-down menu to switch to the spreadsheet view shown in FIG. 4.

Referring now to FIG. 4, the exemplary spreadsheet view 42 includes image management toolbars 50 along a top edge, a spreadsheet image generally below the toolbars and a palette directory 67 along a right-hand edge of the interface 42. Interface 42 presents or is useable to access a second tool subset and, for each tool in the second subset, a second properties subset where the tools and properties can be selected and/or set during an inspection system specifying process. Here, the second tool subset may include all of the tools (albeit in a second form) in the first tool subset and some additional tools and the second properties subset may include all of the properties in the first properties subset and some additional properties. In some embodiments the second tool subset will include essentially all tools needed to specify a vision inspection system or at least all tools supported by the specifying system.

Among other tools, toolbars 50 include view option 69 and a cell expression field 78. The spreadsheet image or representation, like a typical spreadsheet view used in other applications, includes a plurality of columns A, B, C, etc., and a plurality of rows 0, 1, 2, 3, 4, etc. Each cell in the spreadsheet image is identifiable by a column and row combination (e.g. A9, F19, etc.). Various information types may be provided within each cell, including a label (e.g., blob color, minimum area, etc.), a value, an expression such as an equation that references one or more other cells, etc. When a cell is selected, an expression associated with the cell in presented in expression field 78. In some cases a cell expression may include a label (e.g., blob color) or value. In other cases an expression may include references to values in one or more other cells, equations including variables that reference other cells, and so on.

Referring still to FIG. 4, palette 67 includes a functions tab 59 and a snippets tab 61. The functions tab 59, as the label implies, can be selected to list all vision inspection functions separately in a directory format. Here, a specific function can be selected and added to any one of the unoccupied cells within the spreadsheet image. The exemplary functions directory is identified by numeral 63 and includes, among other functions, a blob function, an edge function, a histogram function, etc.

Snippet tab 61 is selectable to access a list (not illustrated) of more sophisticated tools or function sets that include labels, expressions, properties and values that together can be used to instantiate a set of spreadsheet cells and to provide more sophisticated pre-defined inspection function processes. For example, one snippet may comprise a generic template version of cells 84 highlighted in FIG. 4 for counting blobs within an image. Thus, when a count blobs template or snippet is selected, an instance of the template would be instantiated and added to the spreadsheet image including default values for tool properties. Thereafter, a developer can use fields presented within the spreadsheet to customize property values. For example, in FIG. 4, a developer can select or deselect a check box in cell E15 to turn on or turn off a boundary property in cell E14 associated therewith. As another example, the developer can select auto or manual using the field in cell B15 to specify whether or not the threshold mode in cell B14 should be automatic or manual.

Referring to FIGS. 3 and 4, when a developer is viewing one tool instance in space 62 of P&C interface 40 when the developer switches to the spreadsheet interface, the spreadsheet view is presented with the cells associated with the tool instance in space 62 presented and highlighted to help orient the developer within the spreadsheet interface. For instance, in FIG. 3, the Blobs 1 tool instance is shown in space 62. When a developer switches from interface 40 in FIG. 3 to the spreadsheet interface, the Blobs 1 cell set 84 is initially shown and highlighted as shown in FIG. 4. Similarly, when a developer switches from the spreadsheet interface 42 to point-and-click interface 40, the information in space 62 is associated with the tool corresponding to the spreadsheet cell most recently accessed.

In addition to setting or modifying tool property values or settings, the spreadsheet interface 42 can be used to add a property to a tool, delete a property from a tool, modify property value ranges, expose or hide properties of an instance of a P&C tool, change the behavior of an instance of a P&C tool, change default tool properties and behaviors and tie or decouple the behavior of two or more tool instances together. In addition, interface 42 can be used to completely specify entirely new tools needed for a specific vision inspection system. Furthermore, interface 42 can be used to store new tool templates as snippets that can be accessed in the future, either during an ongoing inspection specifying process or during subsequent specifying processes.

Referring once again to FIGS. 2, 3 and 4, when a developer uses interface 40 to add an inspection tool instance to an inspection program, computer 14 converts that selection via converter 41 to spreadsheet data which is automatically added to the spreadsheet specification 39. Thus, for instance, in FIG. 3 where the Blobs 1 instance of the blobs tool has been added to the system, a Blobs 1 snippet (i.e., a specific instance of a count blobs template) 84 is added to the spreadsheet. Thereafter, as the developer uses interface 40 to modify property values and settings via the edit tool space 62, those changes to the Blobs 1 instance are used to modify the Blobs 1 snippet in the spreadsheet specification. Thus, the spreadsheet or spreadsheet specification 39 reflects all of the changes made to the inspection system using either of the point-and-click interface 40 or the spreadsheet interface 42.

Similarly, referring to FIGS. 2-4, when changes are made to cells in the spreadsheet specification 39 via interface 42, if those cells are associated with properties and/or values observable via the point-and-click interface 40, those changes are also reflected in the point-and-click interface 40. For instance, where a developer changes the setting in cell 15B from auto to manual, that change would be reflected in field 41 of interface 40 in FIG. 3. Thus, it should be appreciated that a developer can easily move between interfaces 40 and 42, that all changes to an inspection program specified via interface 40 are reflected in the spreadsheet interface 42 and that at least a subset of the changes made to the program via interface 42 are reflected in the point-and-click interface 40.

Referring again to FIG. 4, in at least some embodiments of the present invention, a developer can use spreadsheet interface 42 to modify tools, ranges, and values that are presented and observable via the point-and-click interface 40. To this end, referring also to FIG. 5, an exemplary process that may be performed by a developer in conjunction with the computer 14 shown in FIG. 1 during an inspection program specifying process as illustrated. At block 122, the developer uses the point-and-click interface or view 40 to specify inspection tools, properties, and property values. At block 124, computer 14 instantiates point-and-click selected tools, properties and values in spreadsheet specification 39 (see also FIG. 2). At decision block 126, computer 14 monitors input by the developer to determine whether or not the program has been completely specified. Where a developer indicates that a program has been completely specified, control passes to block 148 where the computer 14 compiles the spreadsheet information to generate a vision inspection program 47.

Referring again to block 126, where the developer has not indicated that the inspection program specifying process is complete, control passes to block 128. At decision block 128, if the developer has not chosen the spreadsheet view, control passes back up to block 122 where the subprocess including steps 122, 124 and 126 is repeated. When the spreadsheet view is chosen at block 128, control passes to block 130 where computer 14 uses spreadsheet specification 39 to render spreadsheet interface 42 via display screen 20. At block 132, computer 14 again checks whether or not the developer has indicated that the program specifying process has been completed. When the process has been completed, control passes to block 148 where the spreadsheet specification 39 is compiled to generate the vision inspection program 47. At block 132, where program specification is not complete, control passes to block 134.

At decision block 134, spreadsheet interface 42 is used to alter the inspection program. Here, in at least some cases certain spreadsheet modifications will, by default, affect the point-and-click interface 40. For instance, when a sellable new property is added to a tool instance, in at least some embodiments the new property will automatically be observable along with value setting tools (e.g., up and down arrows as part of a range setting field) in the P&C interface. In other cases, by default, spreadsheet modifications will not be observable in the P&C interface. For example, a simple inspection result may, by default, be hidden from view in the P&C interface.

Where a property or result is hidden or exposed in the P&C interface by default, in at least some embodiment a developer is able to modify the default status of the property or result. For instance, where a result is, by default, not shown in the P&C interface, the developer may be able to select the result and manually indicate that the result should be observable via the P&C interface. Where a developer changes the default status of a property/result, a flag is set in the spreadsheet specification 39 to indicate the change.

Figure 5:
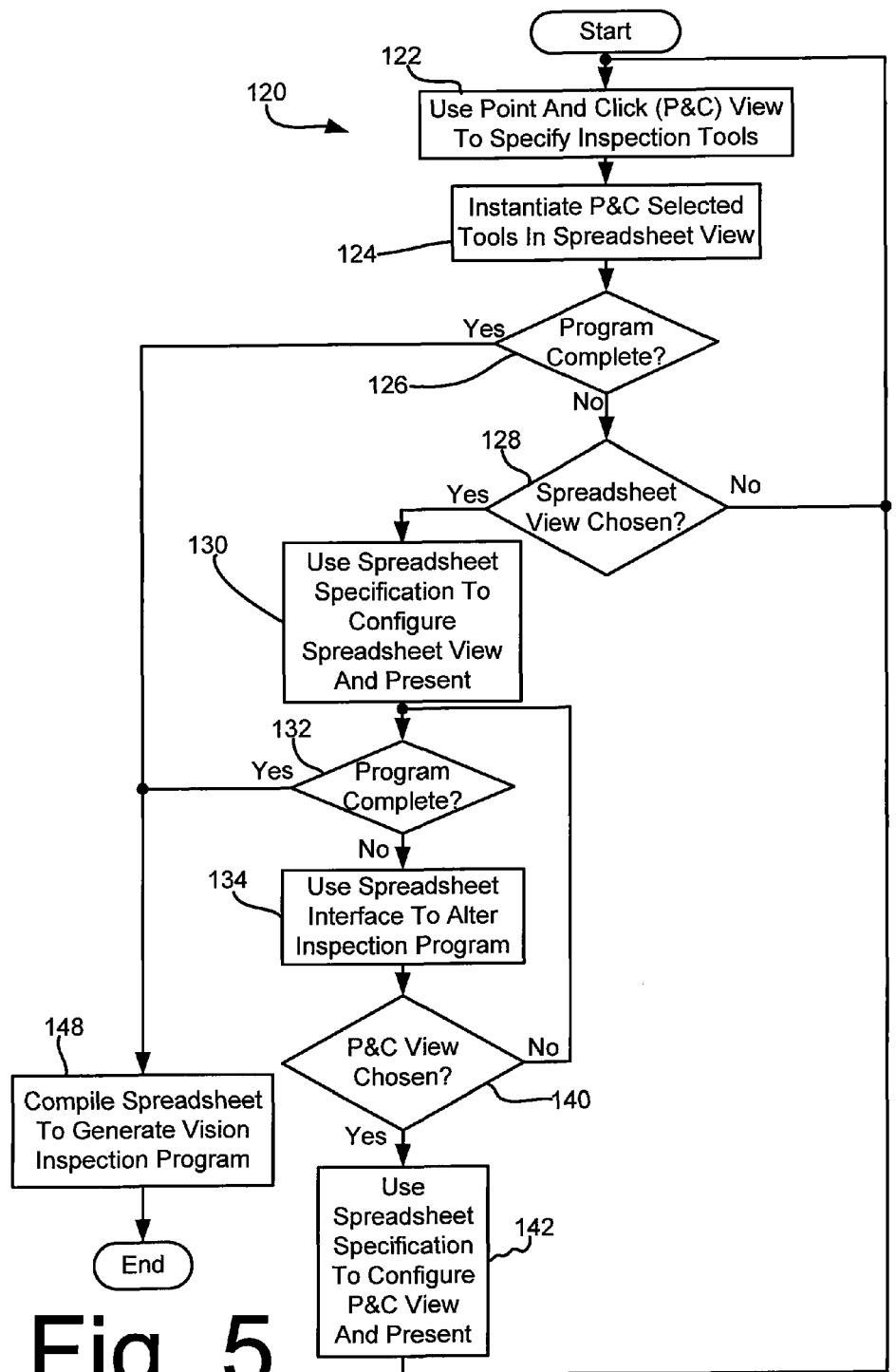
FIG. 5 is a flow chart illustrating a process for specifying an inspection process using a combination of a point-and-click interface and a spreadsheet/scripting interface where changes using either of the two interfaces is reflected in the other of the two interfaces.

Referring still to FIG. 5, at block 140, computer 14 determines whether or not the developer has chosen to switch back to the point-and-click view. Where the developer has not chosen to switch back to the point-and-click view, control passes back up to block 132 where the subprocess including blocks 132 and 134 is repeated. Where the developer has elected to go back to the point-and-click view, control passes from block 140 to block 142 where computer 14 uses the spreadsheet specification 39 to generate the point-and-click interface view (see FIG. 3 again).

Hereafter, several examples are presented wherein the exemplary spreadsheet interface 42 (see FIG. 2) is used to modify tool properties and/or tools presented via the point-and-click interface 40 that should be instructive regarding the power of at least some aspects of the present invention. To this end, the examples include a first example wherein a result is added to a tool, a second example where a property is added to a tool, a third example where a property is deleted from a tool and a fourth example where a generic template snippet is used to define a new inspection tool. Other modifications contemplated but not described in specific examples hereafter include changing the behavior of an instance of a P&C tool, changing default properties and/or behavior of a P&C tool so that future instances thereof will use the new default, and tying and decoupling behavior of two or more tool instances together. Here, the term "behaviors" is used to refer to a process, procedure or method facilitated by the tool.

Figure 6:
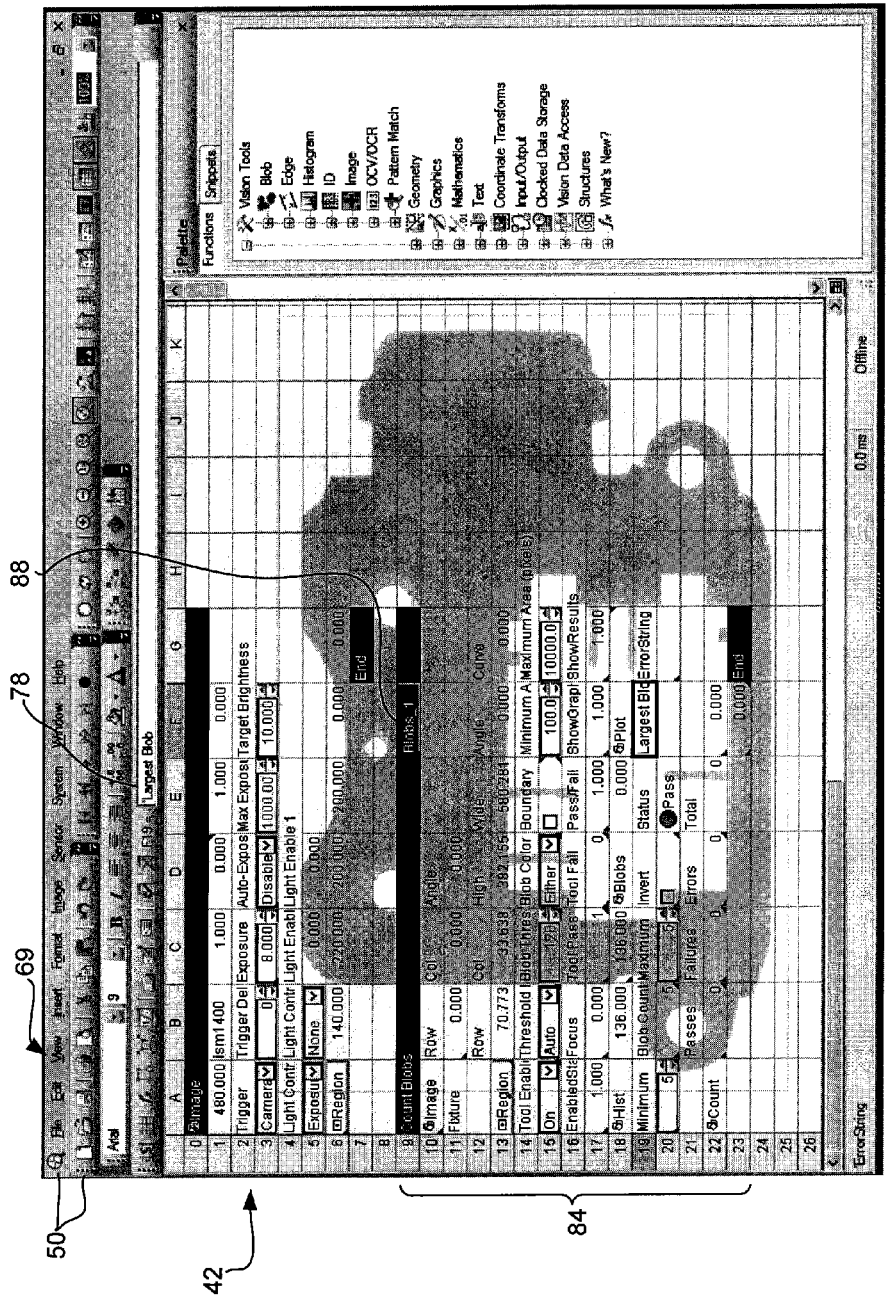
FIG. 6 is a screenshot similar to the screenshot shown in FIG. 4, albeit at a different time during an inspection system specifying process.

Referring once again to FIG. 3, it can be seen that within space 62, when tab 70 is selected, the Blobs 1 tool includes six properties including a Threshold Mode, a Blob Threshold, a Blob Color, a Boundary, a Minimum Area and a Maximum Area. Referring also to FIG. 9, a modified version of interface 40 is shown where a Largest Blob label 110 and result 112 have been added to the Blobs 1 tool properties using the spreadsheet interface as shown in FIGS. 4 and 6-8. More specifically, referring to FIGS. 3 and 4, to switch from the point-and-click interface 40 to the spreadsheet interface 42, as described above, a developer selects view option 69 from tool bar 50 and changes the view from the point-and-click view to the spreadsheet view where the spreadsheet view is shown in FIG. 4. Next, the developer selects a cell within the Blobs 1 cell set 84 to provide a label for the largest blob result to add to the Blobs 1 tool. As shown in FIG. 6, the developer selects cell F19 using a mouse controlled cursor or the like. When cell F19 is selected, the cell is highlighted and an expression associated therewith is presented in cell expression field 78. Initially, as shown in FIG. 4, cell F19 is blank and therefore, initially, the expression field 78 would be blank. In the present case, the developer types in "Largest Blob" in field 78 to provide a label to be added to cell F19 as shown in FIG. 6.

Figure 7:
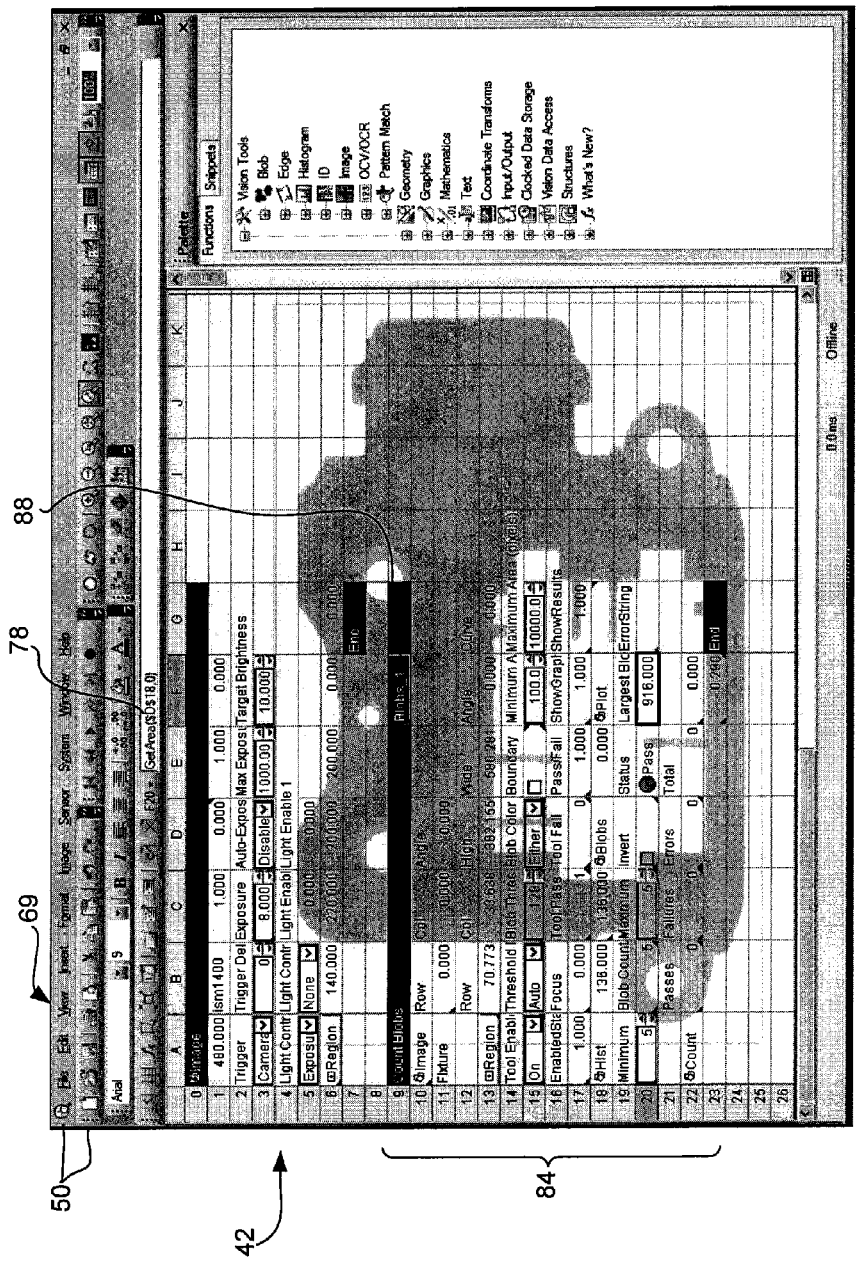
FIG. 7 is similar to FIG. 6, albeit at a different time during a specifying process.

Referring now to FIG. 7, the developer next selects cell F20 which is highlighted and then the developer types in an expression in field 78 corresponding to the highlighted cell F20. The exemplary expression in FIG. 7 includes "Get Area ($D$18,0)" which indicates that the largest blob area corresponding to the Blobs expression in cell D18 should be presented in cell F20. As shown in FIG. 7, a value 916 corresponding to the largest Blobs area from cell D18 is provided within cell F20. In the present example, expressions in one spreadsheet cell are associated with labels thereabove by default unless specified otherwise. Thus, the value in cell F20 corresponds to the label in cell F19. At this point, the largest blob result has been added to the Blobs 1 tool and will be visible in the future when the spreadsheet view 42 is accessed. However, at this point, the largest blob result is not observable when the point-and-click interface is accessed.

Figure 8:
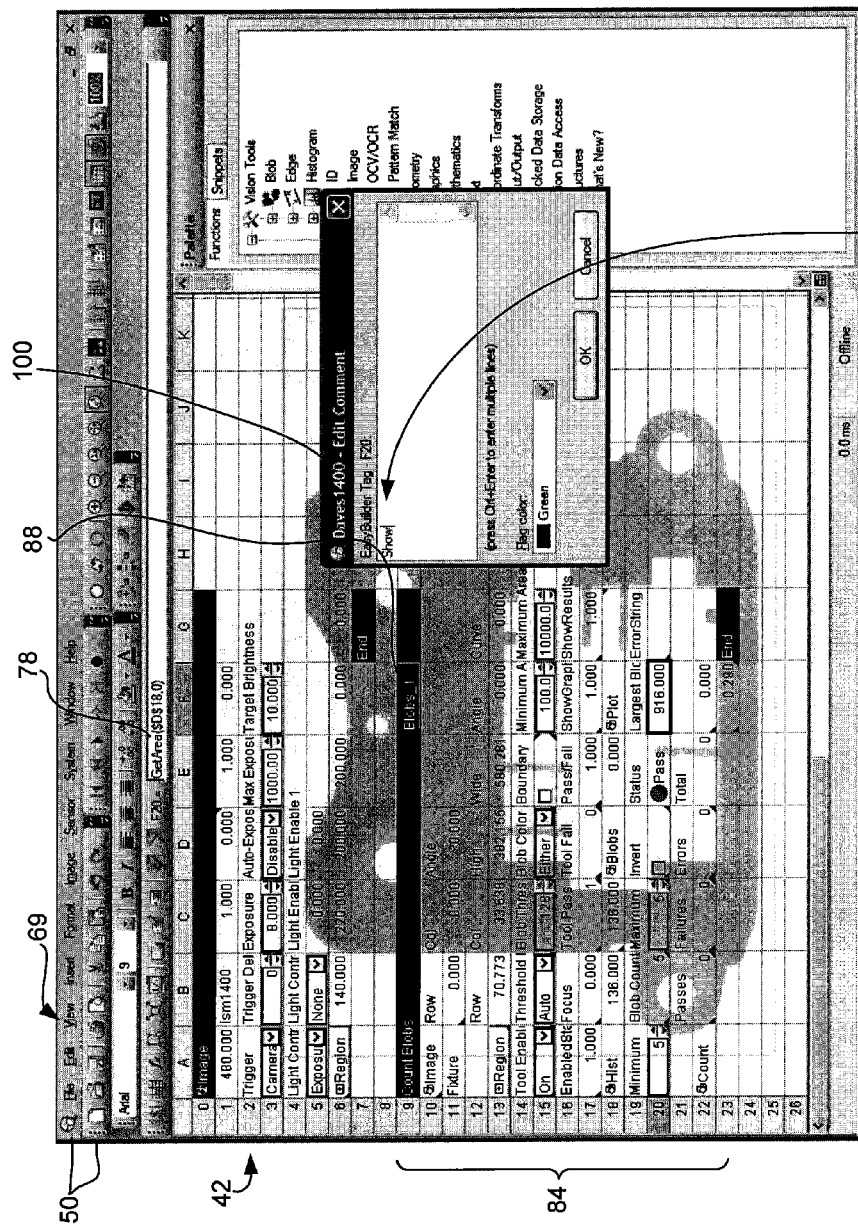
FIG. 8 is similar to FIG. 6, albeit showing a different time during an specifying process.
Figure 9:
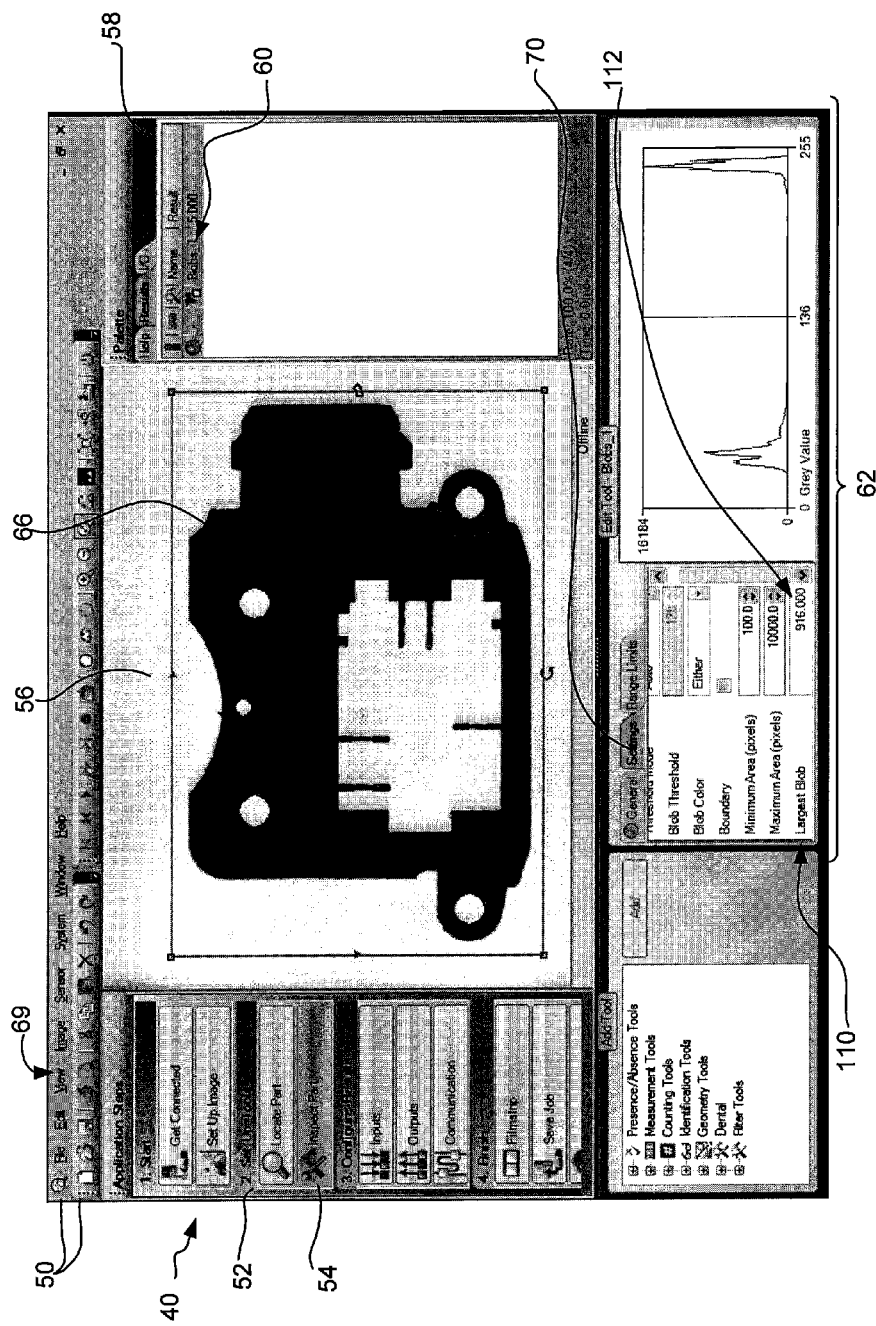
FIG. 9 is similar to FIG. 3, albeit showing a point-and-click type interface after an additional result has been added thereto.

Referring now to FIG. 8, to present the largest Blob result via the point-and-click interface, the developer can right click via a mouse device or the like on cell F20 and open an edit comment window 100 where the developer can enter the term "show" in a field 102 to indicate that the selected result should be shown in the point-and-click interface 40. Here, the default is that any result or property marked to be shown via the point-and-click interface will be shown when the settings tab 70 (see again FIG. 3) is selected. To show a property or result under one of the other tabs 68 or 72 corresponding to the general or range limits properties, a special tag would have to be defined by the developer.

Referring now to FIG. 9, after the developer indicates that the largest Blob results should be shown in the point-and-click interface, when the developer next accesses a point-and-click interface and the settings tab 70 corresponding to the Blobs 1 tool, the largest blob label 110 and result 112 are presented along with the properties associated with the Blobs 1 tool.

Figure 10:
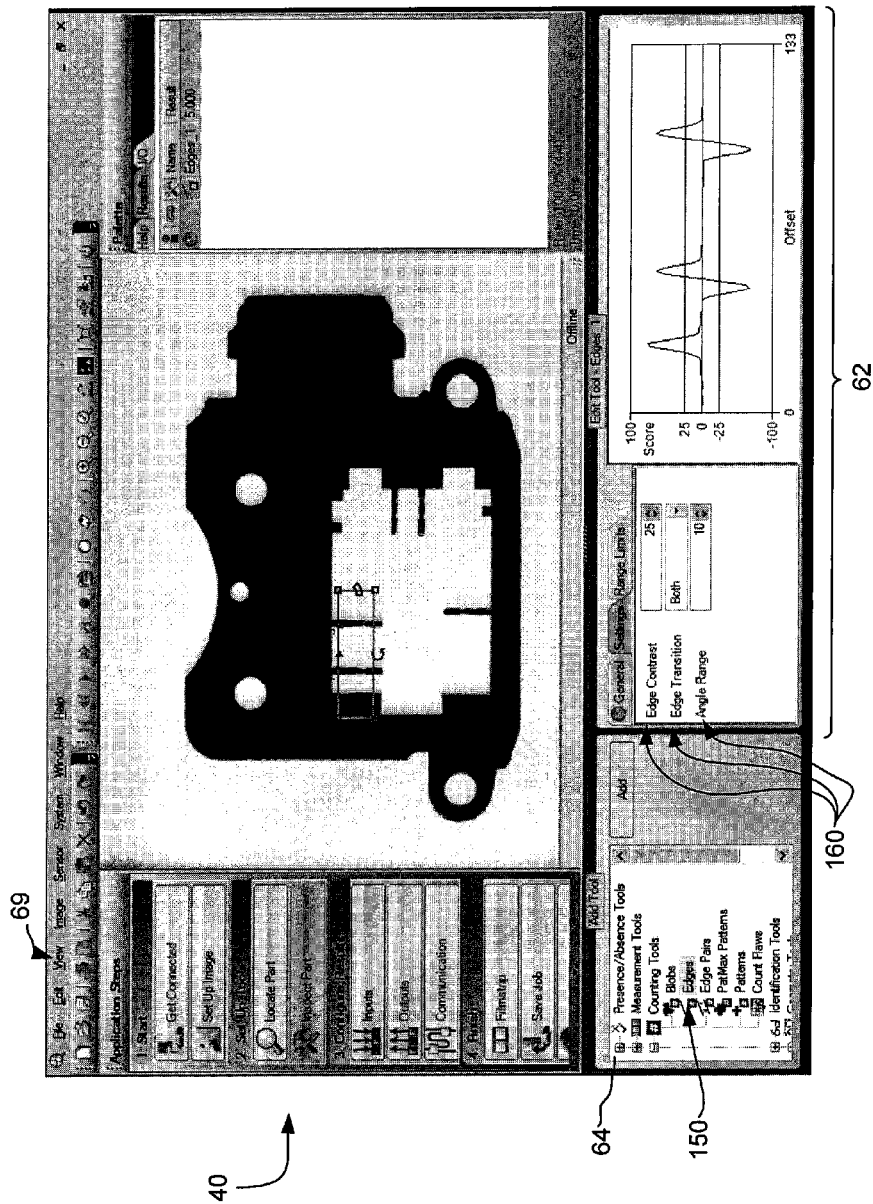
FIG. 10 is similar to FIG. 3, albeit showing a different time during a specifying process.
Figure 14:
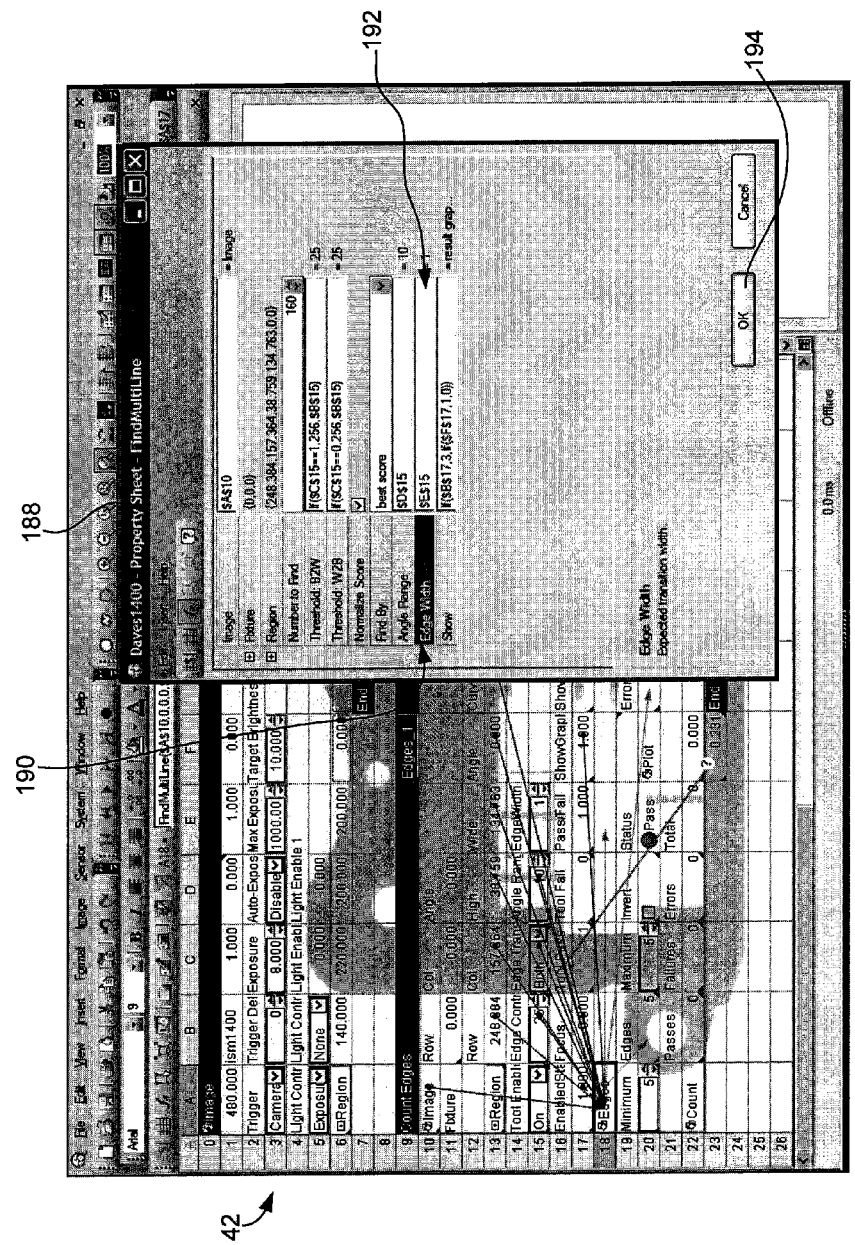
FIG. 14 is similar to FIG. 6, albeit showing the interface at yet another time during the specifying process.
Figure 15:
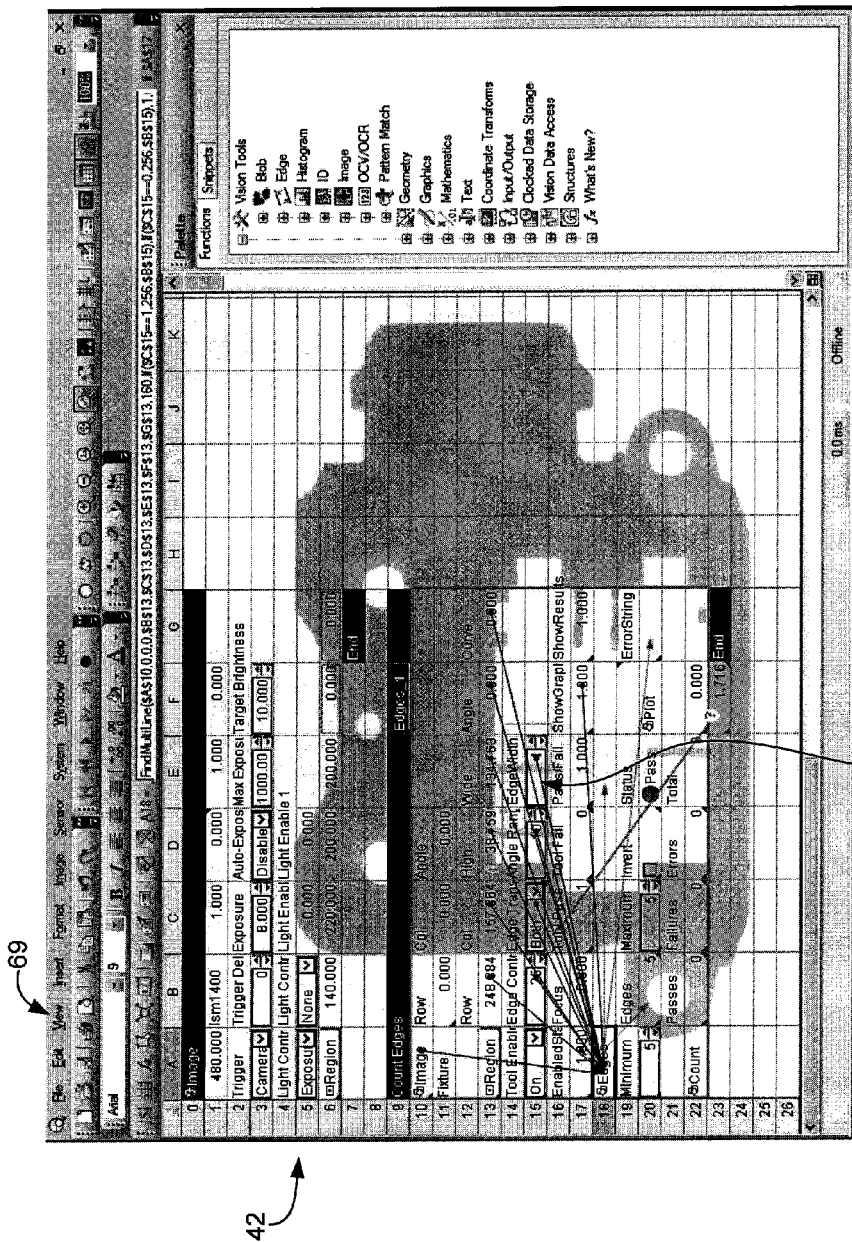
FIG. 15 is similar to FIG. 6, albeit showing the interface at yet another time during the specifying process.
Figure 16:
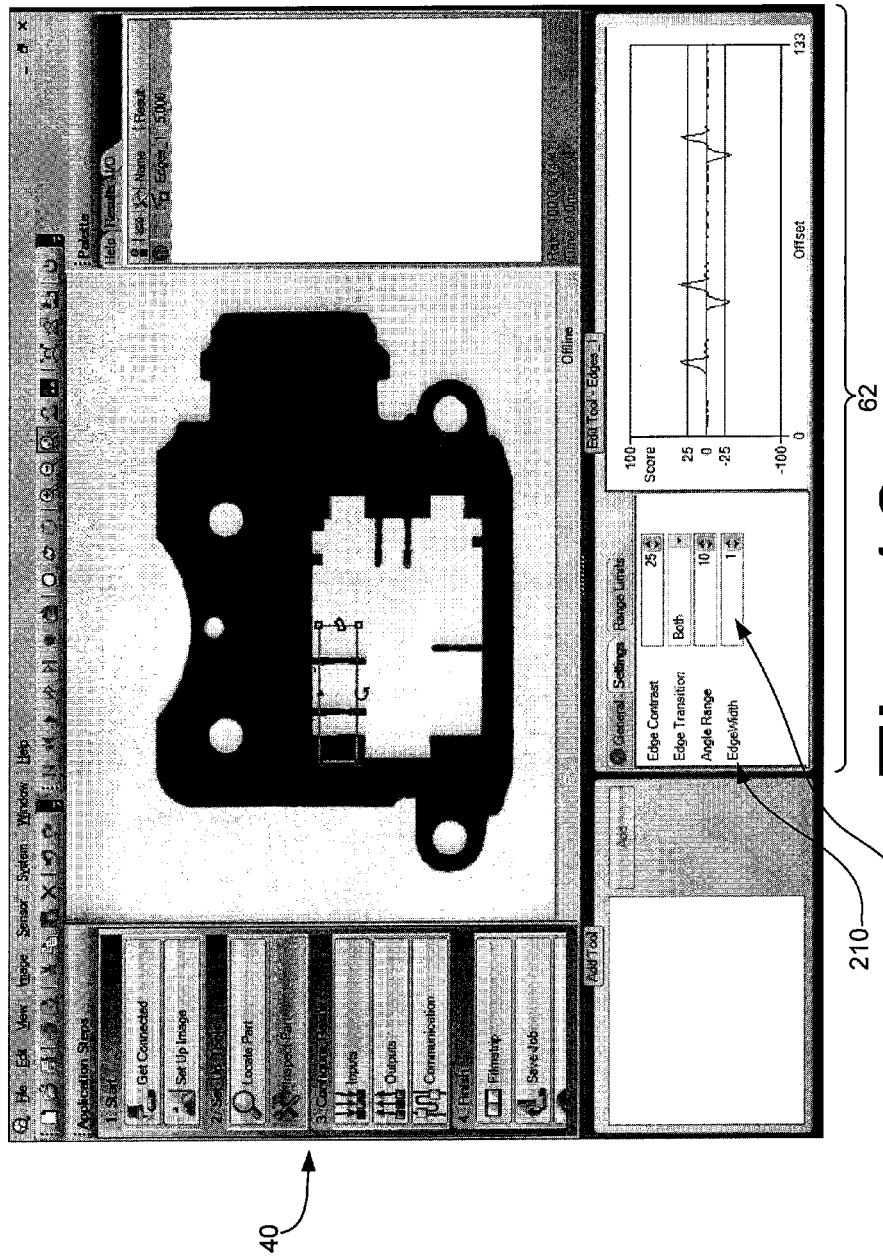
FIG. 16 is similar to FIG. 10, albeit showing a point-and-click interface after an additional property and value field have been added.

Referring now to FIGS. 10-16, an exemplary process will be described whereby a property is added to an Edges 1 tool. Referring specifically to FIG. 10, when the Edges tool option 150 is selected from menu 64, Edges 1 properties are presented within space 62. Presented properties in space 62 include Edge Contrast, Edge Transition and Angle Range which are collectively identified by numeral 160. Referring also to FIG. 16, after the process to be described next, a fourth property label Edge Width 210 and value field 212 associated therewith are provided in representation 62.

Figure 11:
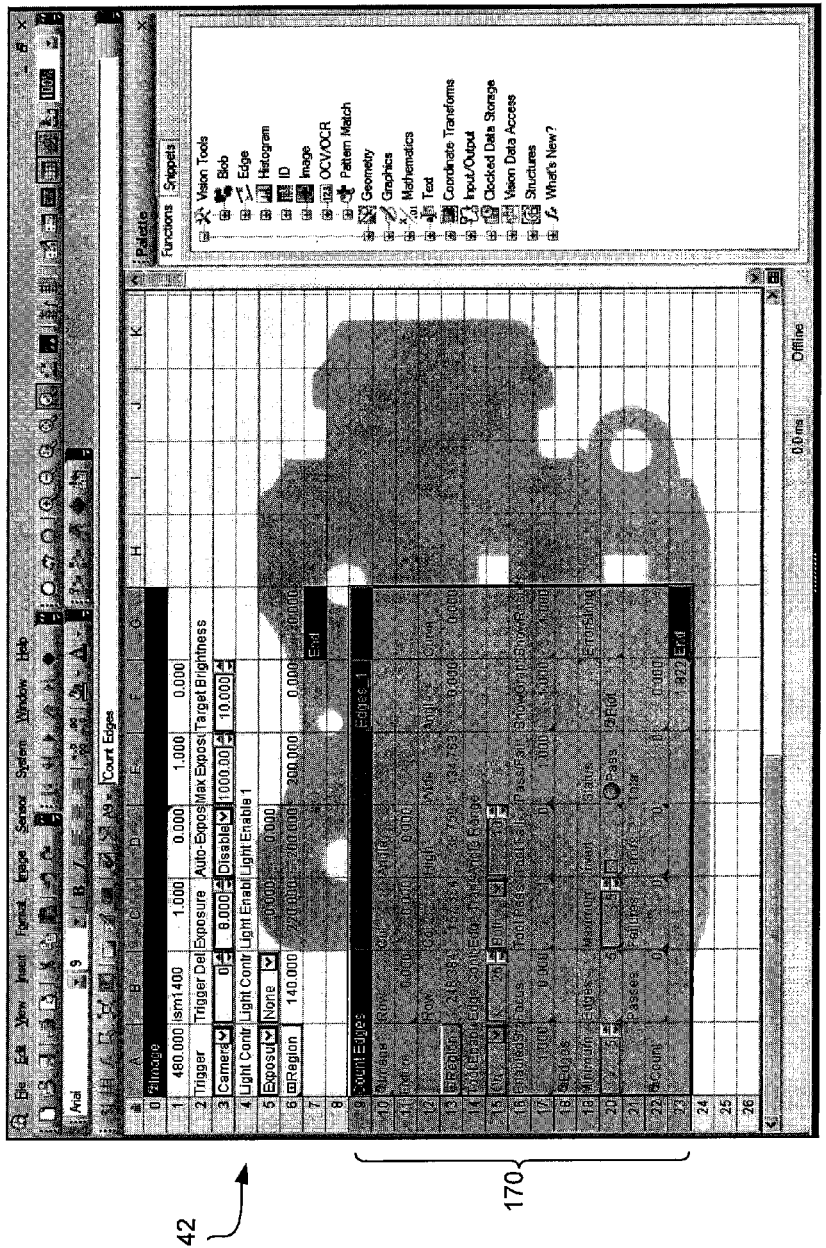
FIG. 11 is similar to FIG. 6, albeit showing a spreadsheet interface at a different time during an inspection system specifying process.
Figure 12:
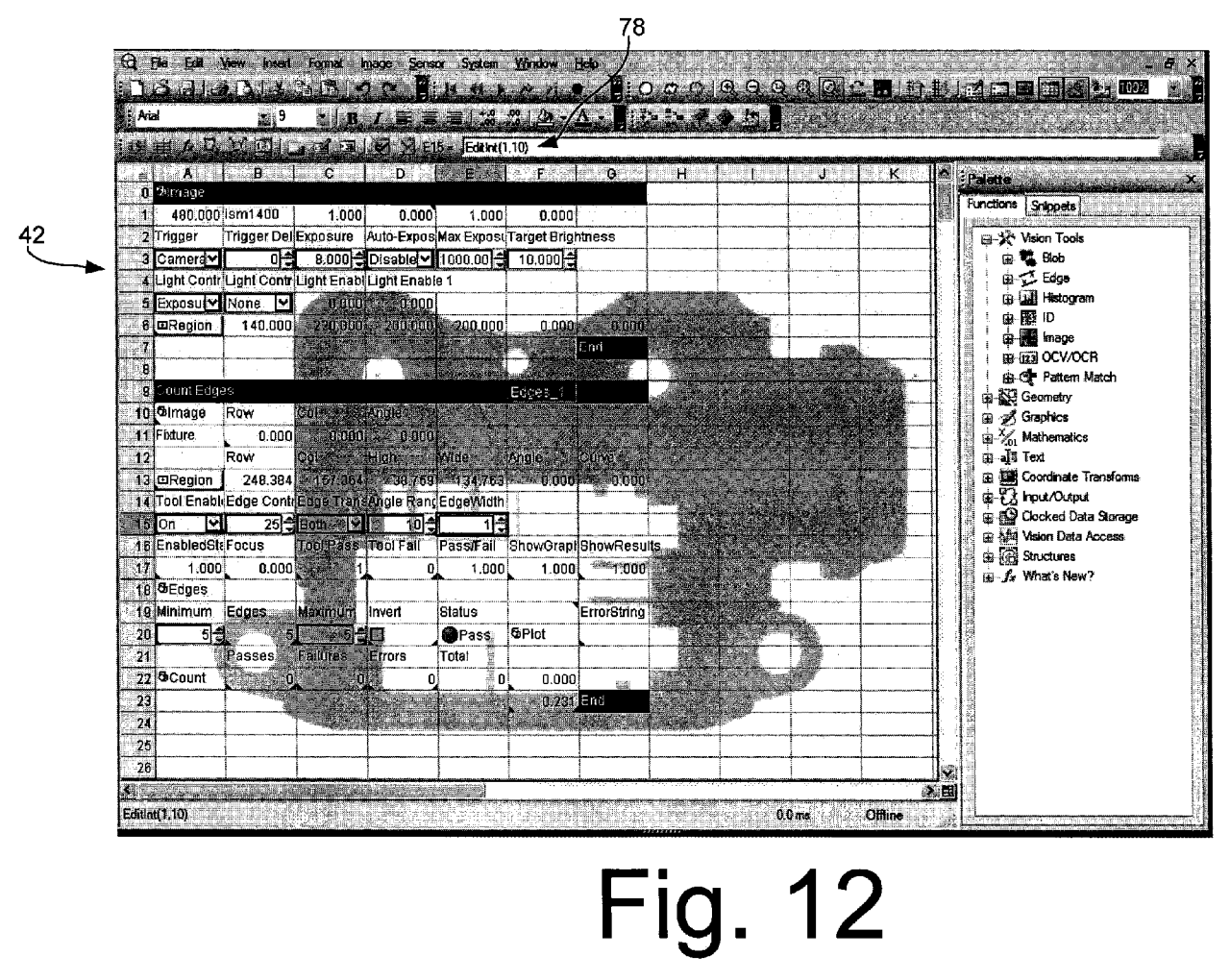

Referring again to FIG. 10, when the spreadsheet interface option is selected from a pull down menu associated with view option 69, the exemplary spreadsheet view 42 shown in FIG. 11 is presented where cells associated with the Edge 1 tool are highlighted as indicated at 170. In FIG. 11, the Edge Contrast, Edge Transition and Angle Range labels corresponding to labels 160 in FIG. 10 are shown in cells B14, C14 and D14, respectively, where range setting fields are specified thereunder in cells B15, C15 and D15, respectively. To add another property and range setting field to the spreadsheet interface, as shown in FIG. 12, a developer selects cell E14 and types in the label Edge Width and then selects cell E15 (shown highlighted in FIG. 12) and enters an expression in field 78 for that cell. As shown in FIG. 12, the expression in field 78 corresponding to cell E15 is "edit int (1,10)" which is recognized by computer 14 as meaning that a range setting field having a range of values between 1 and 10 should be provided in cell E15. The exemplary range setting field is shown in cell E15 in FIG. 12.

Figure 13:
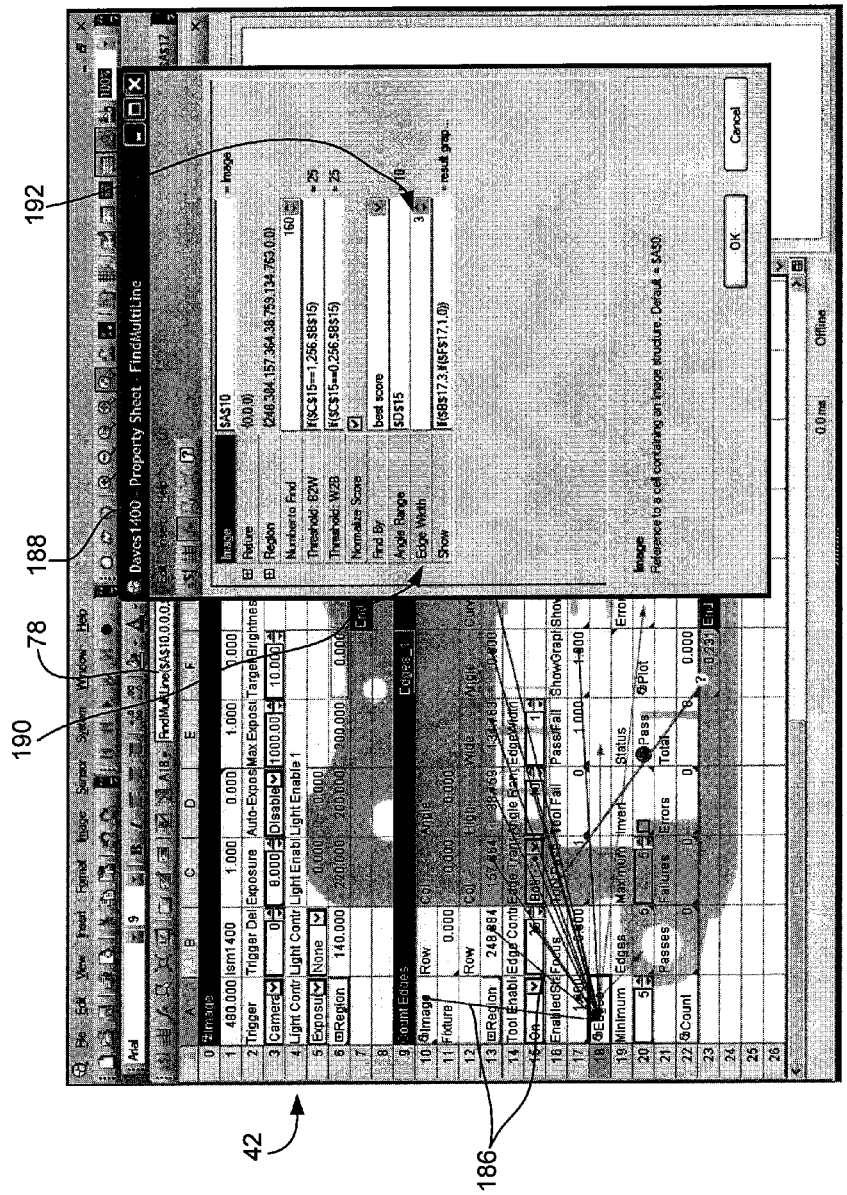
FIG. 13 is similar to FIG. 6, albeit showing the interface at yet another time during the specifying process.

Next, referring to FIG. 13, the developer selects cell A18 corresponding to an Edge expression causing the spreadsheet interface to highlight cell A18. By double-clicking on cell A18, dependencies for that cell can be indicated via dependency lines, two of which are collectively identified by numeral 186. Here, the dependencies lines indicate other cells that the expression associated with cell A18 are related to either through the cell A18 expression referencing the other cell or through some other cell referencing at least a portion of the expression associated with cell A18. Double clicking on any other spreadsheet cell in interface 42 would cause similar dependency lines to be added in the interface 42.

As seen best in FIG. 15, when cell A18 is selected, a long and complex expression (only part shown) is provided in expression field 78. Referring again to FIG. 3, by right-clicking on cell A18, a property sheet pop-up window 188 is opened which includes a list of properties and sub-expressions associated therewith where the combination of properties and sub-expressions correspond to the complex expression in field 78. In short, window 188 presents the complex expression in a simplified format that is easier for a developer to understand and use. As shown in FIG. 13, one property and field associated with the Edges expression in cell A18 includes Edge Width 190 and field 192. In FIG. 13, a default edge width of 3 is presented in field 192. Referring now to FIG. 14, the developer references cell E15 in field 192 to indicate that the edge width for the expression associated with cell A18 should be obtained from the value selected using the range setting field in cell E15. Thereafter, the developer selects icon 194 to complete the selection. Once the selection is completed, as shown in FIG. 15, a dependency line 200 extends from cell E15 to the edges cell A18 indicating a dependency (i.e., that cell A187 depends at least in part on the value selected via cell E15).

Here, all properties specified within cells corresponding to the Edges 1 tool are automatically presented via the point-and-click interface so that there is no need to manually set a flag to show the property and the associated value field. Thus, referring to FIG. 16, after the edge width property and associated range setting field have been specified via the spreadsheet interface, when the point-and-click interface is accessed, the property label 210 and associated field 212 are presented within space 62.

Referring now to FIG. 3, an exemplary process for eliminating the boundary property 75 and corresponding check box 43 from interface 40 will be described. After the boundary property and corresponding box are removed, the point-and-click interface 40 will have the appearance shown in FIG. 20.

Figure 17:
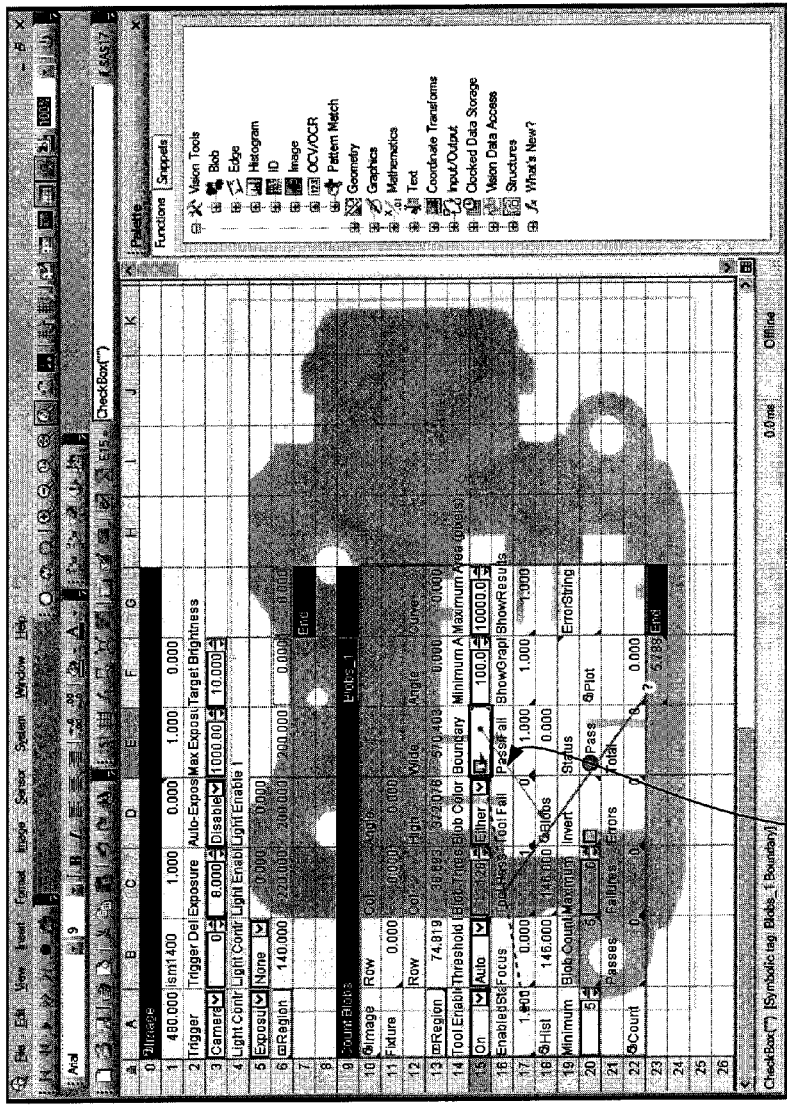
FIG. 17 is similar to FIG. 6, albeit showing the spreadsheet interface at a different time during the specifying process.
Figure 18:
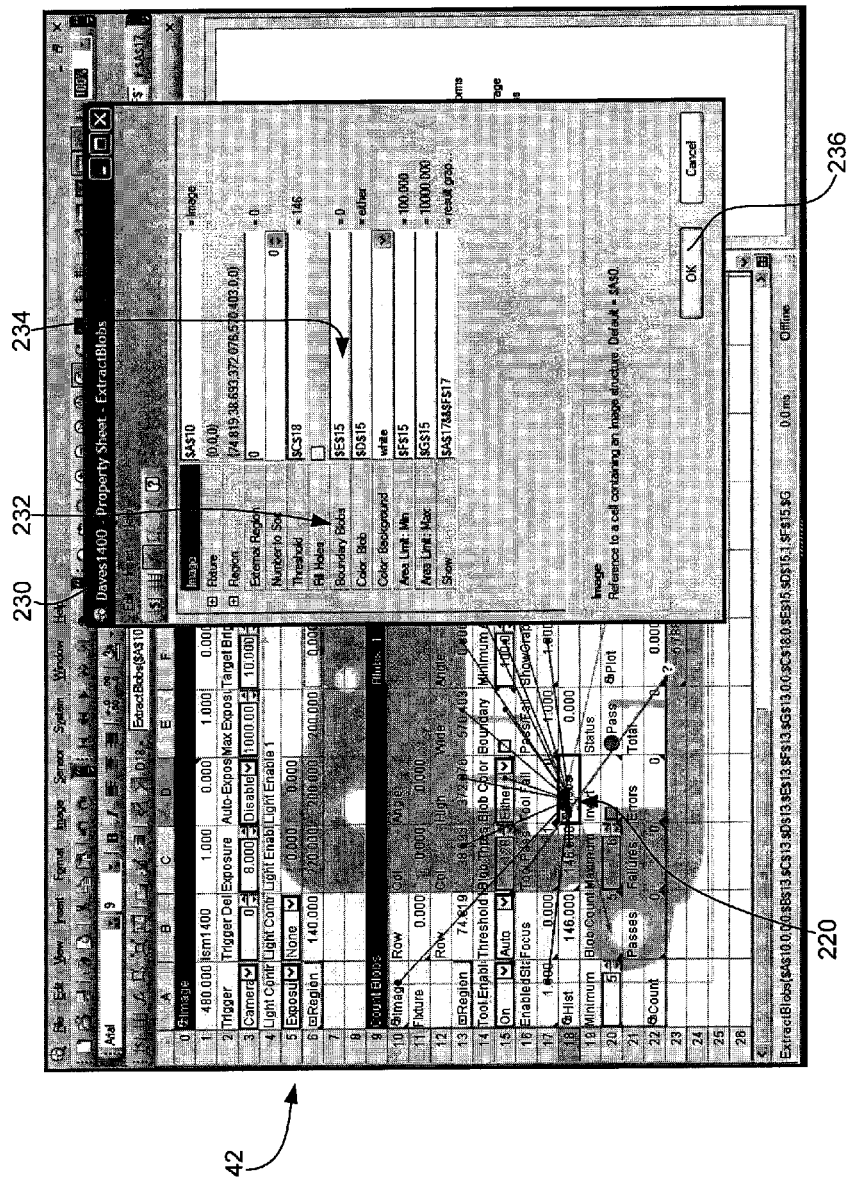
FIG. 18 is similar to FIG. 6, albeit showing the interface at a different time during the specifying process.
Figure 19:
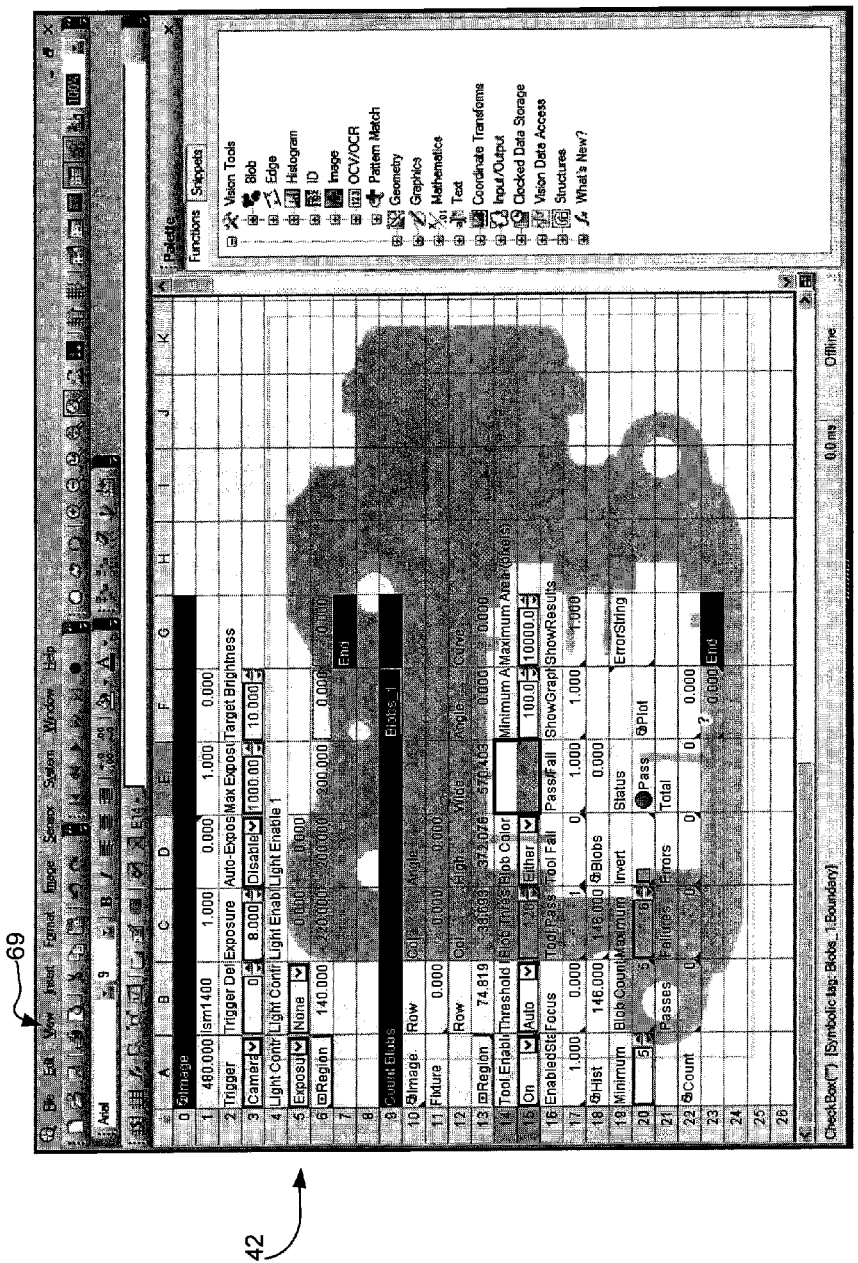
FIG. 19 is similar to FIG. 6, albeit showing the interface at a different time during the specifying process.
Figure 20:
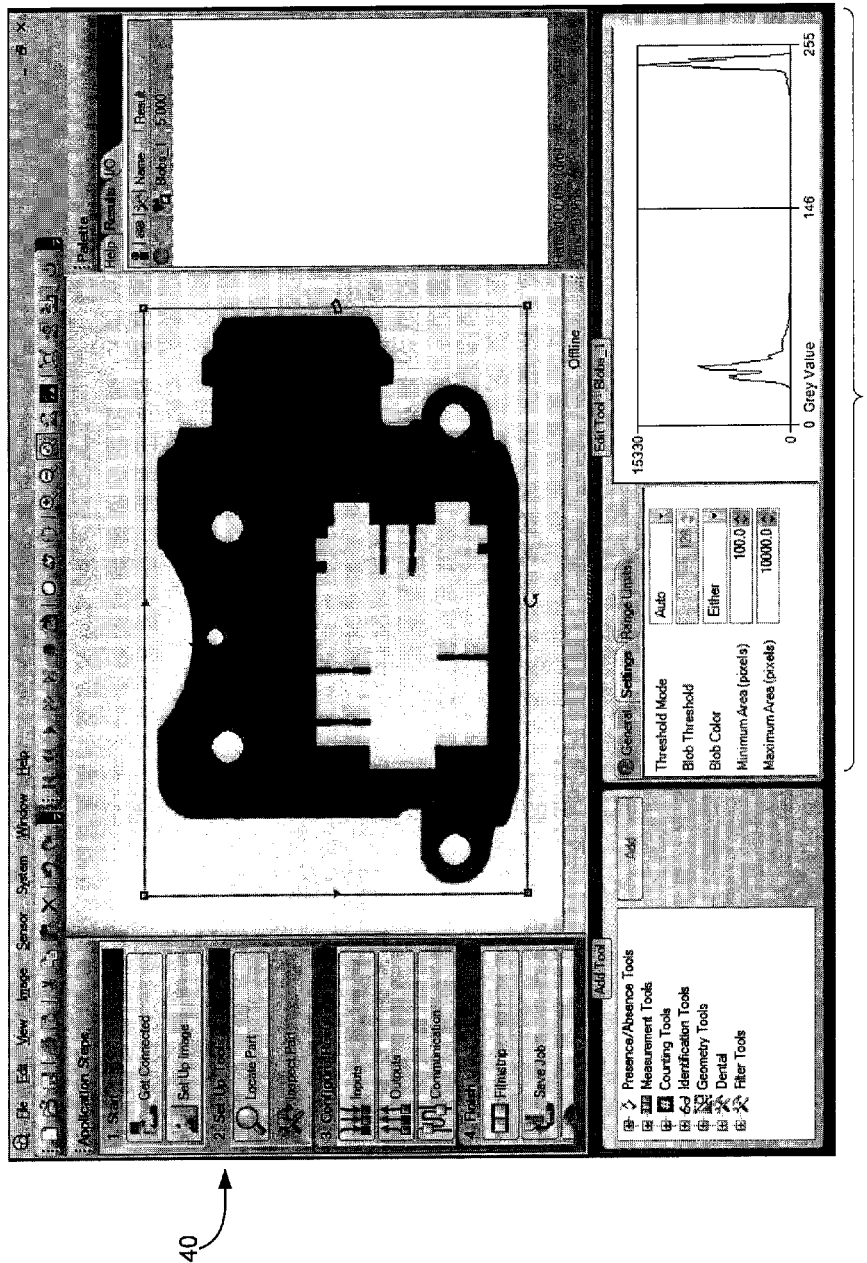
FIG. 20 is similar to FIG. 3, albeit showing the point-and-click interface at a different time after a boundary property and corresponding selection box have been removed from the interface.

Referring now to FIGS. 3 and 17, when the developer switches from the point-and-click interface 40 to the spreadsheet interface 42 and views the cells 84 corresponding to the Blobs 1 tool, the boundary label and associated selection box are presented in cells E14 and E15, respectively. By double-clicking on the selection box cell E15, the developer causes the interface to add dependency lines associated therewith to the interface 42 including line 220 that indicates that the value of the selection box from cell E15 is used in the expression associated with the Blobs cell D18. Referring to FIG. 18, double-clicking on the Blobs cell D18 causes dependency lines associated therewith to be added to the spreadsheet interface and right-clicking on cell D18 causes properties sheet pop-up window 230 to open where window 230 includes properties and associated fields usable to modify the expression associated with cell D18. As shown in FIG. 18, the boundary blobs property 232 is initially associated with cell E15 as shown in field 234. The developer blanks out field 234 to eliminate the dependency of the blobs expression from cell D18 on the state of cell E15 and then selects OK icon 236. Next referring to FIG. 19, the developer blanks out cells E14 and E15 to get rid of the boundary label and associated selection box. At this point, the boundary property no longer appears on the spreadsheet interface 42m. Here, the default is that properties removed from the spreadsheet interface are also automatically removed from the point-and-click interface. As shown in FIG. 20, the boundary label and corresponding field (see 75 and 43 in FIG. 3) have been eliminated from the point-and-click interface.

Figure 21:
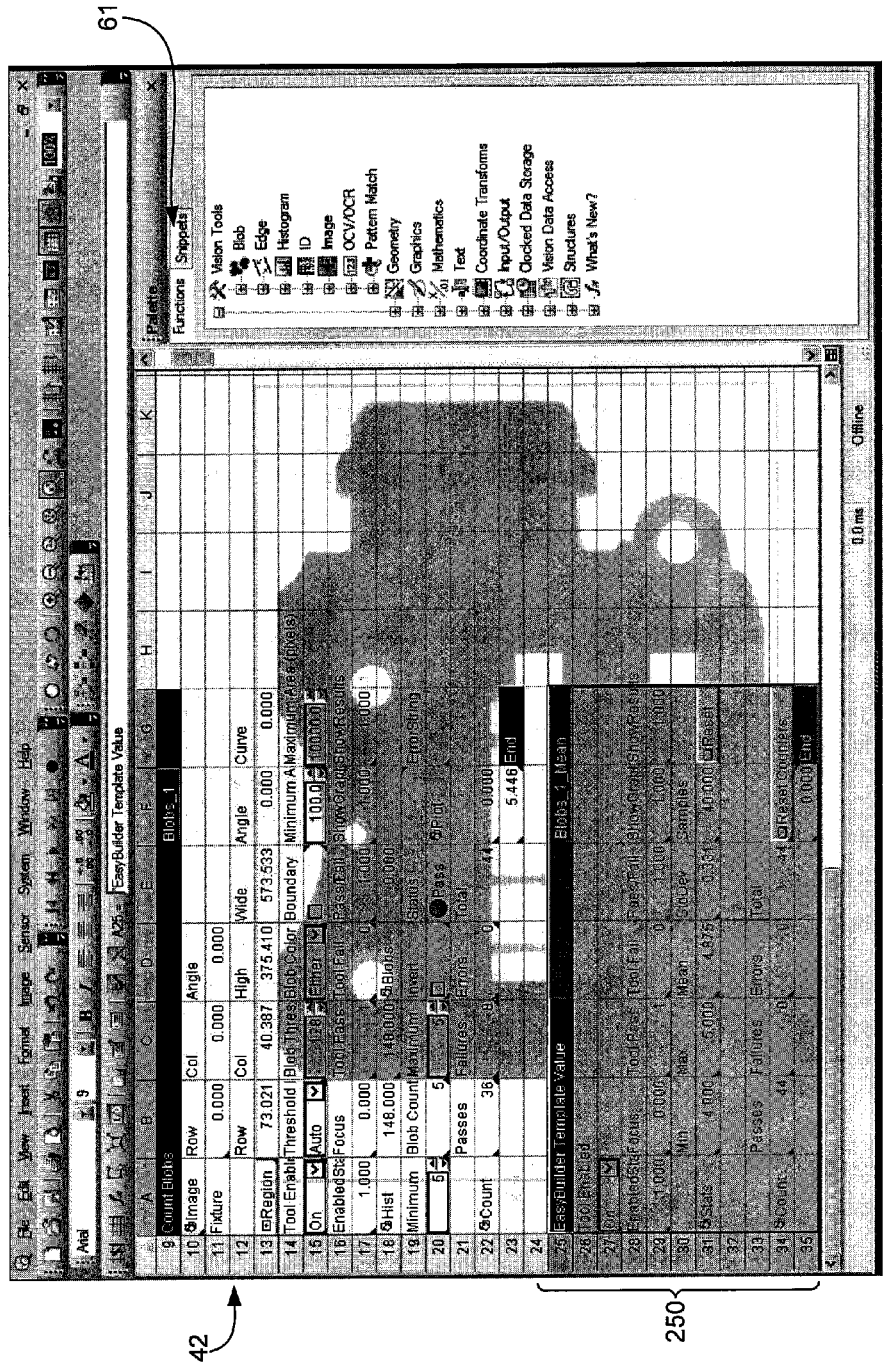
FIG. 21 is similar to FIG. 6, albeit showing the spreadsheet interface after a standard template for specifying a new tool has been selected and customized to some extent.

In addition to adding results to and deleting results from a point-and-click interface using a spreadsheet and adding properties to and deleting properties from a point-and-click interface using a spreadsheet interface, in at least some embodiments, it is contemplated that completely new tools may be added to a point-and-click interface using a spreadsheet interface. To this end, referring to FIG. 21, a developer may select a standard template snippet from the directory (not illustrated) associated with the snippet tab 61 to instantiate an instance of the template as a new cell set template within the spreadsheet interface 42. In FIG. 21, an exemplary instantiated instance of a template is shown at 250 where various properties and expressions have already been added to the template to customize the template as a Blobs 1 Mean tool. Here, a statistic expression associated with cell A31 defines, among other statistics, a minimum value, a maximum value, a mean value, a standard deviation and a samples count value. The developer has added labels Min, Max, Mean, Std Dev and Samples to cells B30, C30, D30, E30 and F30, respectively. Expression have been added to each of cells B31, C31, D31, E31 and F31 that reference the minimum, maximum, mean, standard deviation and sample count values from the statistics expression in cell A31. Here, the values in cells B31 through F31 correspond to the labels in cells B30 through F30, respectively.

It is assumed that the developer has manually used to spreadsheet interface to indicate that each of the results in cells B31 through F31 should be shown when the Blobs 1 Mean tool is accessed via the point-and-click interface 40.

Figure 22:
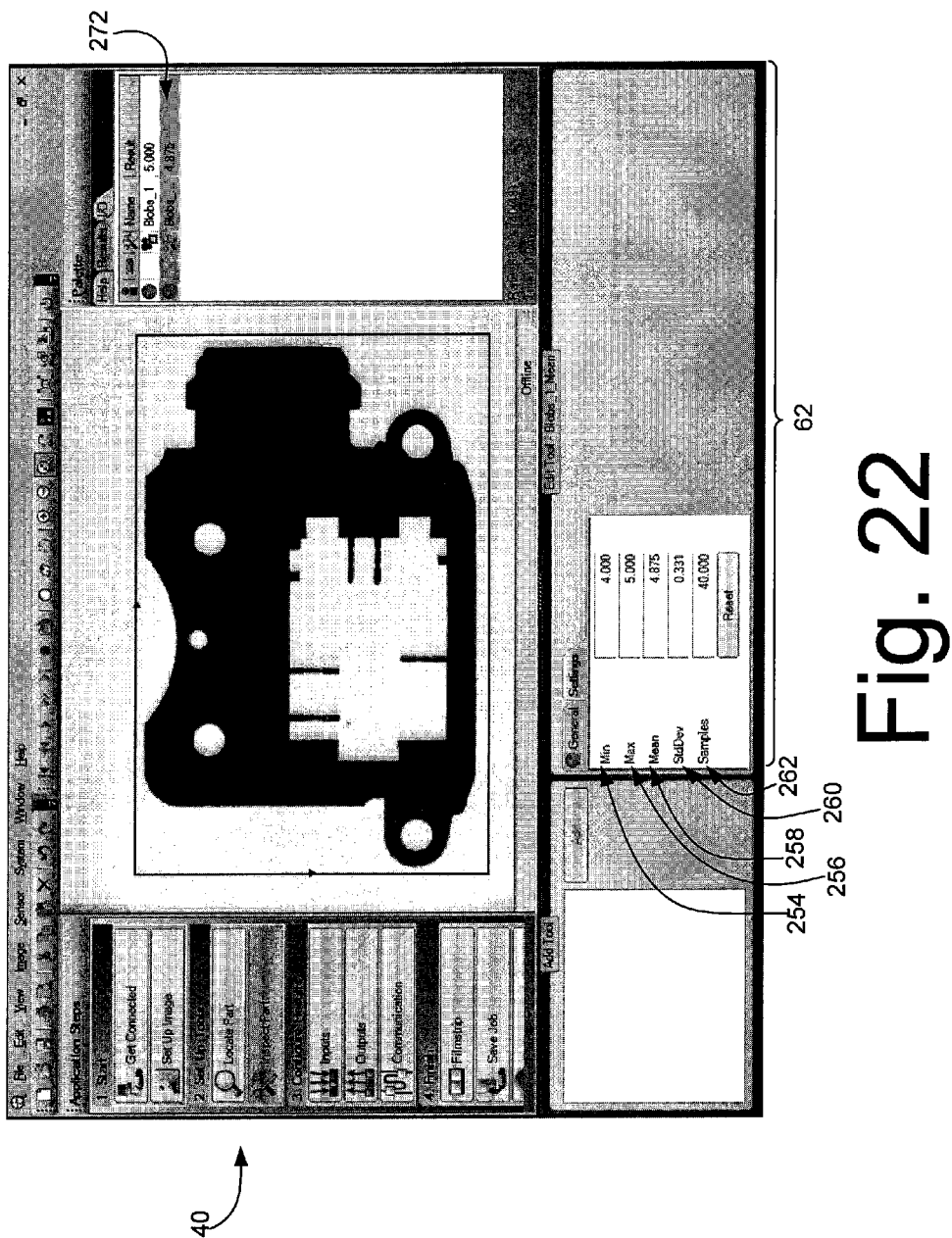
FIG. 22 is similar to FIG. 4, albeit where a new tool is being presented that corresponds to the instance of the template shown in FIG. 21.

When the developer switches from the spreadsheet interface 42 to the point-and-click interface 40 shown in FIG. 22, the Blobs 1 Mean tool information is presented in space 62 including the Minimum, Maximum, Mean, Standard Deviation and Sample count labels 254, 256, 258, 260 and 262, respectively, as well as fields associated with each one of those labels in which values are presented. Thus, a blobs statistics tool has been defined and exposed for use as part of the point-and-click interface 40.

Figure 23:
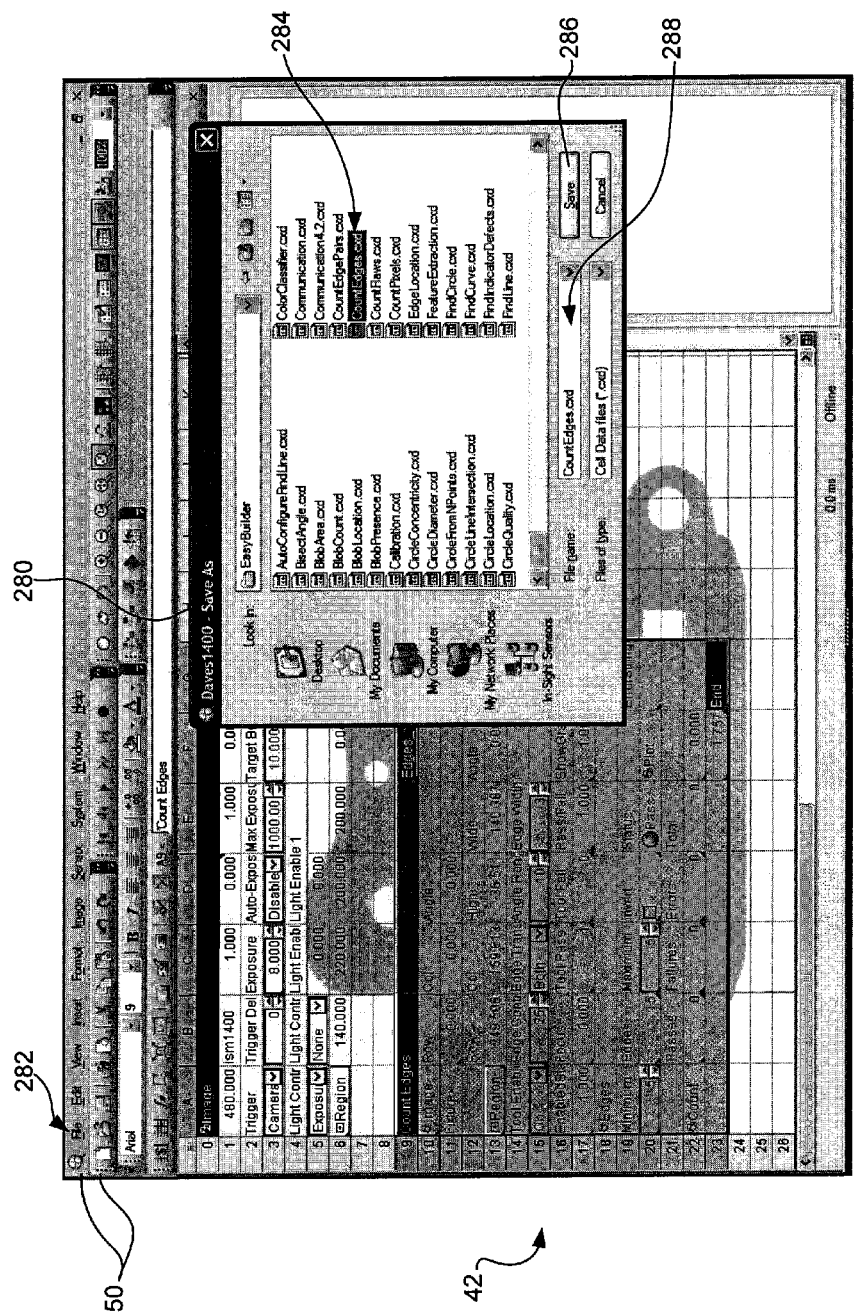
FIG. 23 is a view similar to FIG. 4, albeit where a "save as" pop up window has been opened.

In at least some embodiments it is contemplated that after a tool has been modified or after a new tool has been specified, a developer may save the tool for use during subsequent specifying processes. To this end, referring again to FIG. 15, once the edge width label and range setting field have been added to cells E14 and E15, respectively, and field E15 has been associated with the expression in cell A18 (see again FIG. 14), the developer can select cell A9 to highlight all cells associated with the Edges 1 tool instance as shown in FIG. 23. Next, the developer can elect to save the modified Edges 1 tool instance over an existing Count Edges snippet file by accessing a "Save As" pop-up window 280 via the file option 282 in tool bar 50, selecting the Count Edge file 284 and then selecting a save button 286. Here, the modified Edges 1 tool is saved as the new Count Edge file for subsequent use.

In a similar fashion, referring again to FIG. 23, a developer could simply enter a new file name for the highlighted tool cells in file name field 288 and select save button 286 to save a new tool template snippet. Here, the new template snippet could be used during an on going program specifying process or during subsequent specifying processes. Where a new template snippet is added to the snippet set, in at least some embodiments, the new snippet is option is reflected in the point-and-click interface by default. In other cases a new snippet is, by default, hidden on the point-and-click interface. In either case the default can be altered by the developer.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

To apprise the public of the scope of this invention, the following claims are made:

1. A programming system for specifying vision inspection tools for a vision inspection system, the programming system comprising:
   a processor;
   a display screen for presenting interfaces to a developer; and
   an input device for receiving information from the developer, the received information specifying the vision inspection system;
   wherein the processor is programmed to provide:
   (i) a first interface including a first view of the vision inspection system as the inspection system is being specified, the first interface usable to at least one of select, from a first tool subset, a first selected set of vision inspection tools to be used in the vision inspection system, and set tool properties in a first properties subset for each of a plurality of vision inspection tools; and (ii) a second interface including a second view of the vision inspection system as the inspection system is being specified, the second interface usable to at least one of select, from a second tool subset, a second selected set of vision inspection tools to be used with the vision inspection system, and set tool properties in a second properties subset for each of the tools in the second tool subset, the second interface also usable to specify script expressions for the vision inspection system that cannot be specified using the first interface;

wherein, upon the selection of a first selected tool for one of the first and second selected sets of vision inspection tools using, respectively, one of the first and second interfaces, an instance of the first selected tool is added to the vision inspection system being specified;

wherein, upon the setting of a tool property for at least one tool included in one of the plurality of vision inspection tools and the second tool subset using, respectively, one of the first and second interfaces, a corresponding property of an associated vision inspection tool in the vision inspection system being specified is set;

wherein, the second interface and the first interface can be used to observe the second view and the first view of the vision inspection system, respectively, during the specifying of the vision inspection system;

wherein, at least a first subset of changes made to the vision inspection system using the first interface are represented as changes to the second interface and at least a second subset of changes made to the vision inspection system using the second interface are represented as changes to the first interface, the first subset of changes including, at least in part, one of the selection of the first selected set of vision inspection tools and the setting of tool properties in the first properties subset, the second subset of changes including, at least in part, one of the selection of the second selected set of vision inspection tools and the setting of tool properties in the second properties subset; and wherein the first interface is a point-and-click interface and the second interface is a spreadsheet interface.

2. The system of claim 1 wherein the first interface is usable both to select the first selected set of vision inspection tools to be used with the vision inspection system from the first tool subset and to set the tool properties in the first properties subset for each of the tools in the first tool subset.

3. The system of claim 2 wherein the second interface can be used to expose and hide properties of an instance of a tool on the first interface.

4. The system of claim 2 wherein the second interface can be used to modify at least one of the first tool subset, the first properties subset, and values associated with the tool properties in the first properties subset.

5. The system of claim 4 wherein the second interface can be used to modify each of the first tool subset and the first properties subset.

6. The system of claim 4 wherein the second interface can be used to modify the first tool subset by at least one of adding a tool to the first tool subset and deleting a tool from the first tool subset.

7. The system of claim 1 wherein the first tool subset only includes a subset of the tools in the second tool subset.

8. The system of claim 7 wherein the second tool subset includes all of the tools available for specifying a vision inspection system.

9. The system of claim 1 wherein inspection program expressions and values corresponding to inspection tools included in the second tool subset are presented in cells of the spreadsheet interface.

10. The system of claim 9 wherein the spreadsheet interface specifies cell set templates for at least a templated subset of the inspection tools included in the second tool subset where, when an inspection tool of the templated subset is selected using either one of the first interface and the second interface, an instance of a cell set template associated with the selected inspection tool of the templated subset is added to the second view.

11. The system of claim 10 wherein at least a subset of the cell set templates include properties that may be accessed via the first interface and wherein the second interface can be used to render the properties accessible or inaccessible via the first interface.

12. The system of claim 1 wherein the second interface can be used to modify an existing tool and to store a new cell set template including cells that reflect changes to the existing tool, where the new cell set template can be used subsequently to instantiate another instance of a tool having properties consistent with the new cell set template.

13. The system of claim 1 wherein the second interface can be used to create a new vision inspection tool and to store a new cell set template including cells that specify the new tool, the second interface also usable to render the new tool accessible via the first interface.

14. The system of claim 1 wherein a first set of changes to a vision inspection system made using the second interface are represented in the first interface and a second set of changes to the vision inspection system made using the second interface do not alter the first interface.

15. The system of claim 1 wherein each change made to the vision inspection system using the first interface is represented in the second interface.

16. The system of claim 1 wherein the first and second interfaces are presented via the display screen independent of each other.

17. The system of claim 1 wherein the first and second interfaces are presented via the display screen at different times.

18. A programming system for specifying vision inspection tools for a vision inspection system, the programming system comprising:

a processor;

a display screen for presenting interfaces to a developer;

an input device for receiving information the developer, the received information specifying the vision inspection system;

the processor is programmed to provide:

(i) a first interface including a first view of the vision inspection system as the inspection system is being specified, the first interface usable to select, from a first tool subset, a first selected set of vision inspection tools to be used in the vision inspection system and to set tool properties in a first properties subset for each of the tools in the first tool subset; and (ii) a second interface including a second view of the vision inspection system as the inspection system is being specified, the second interface usable to select, from a second tool subset, a second selected set of vision inspection tools to be used with the vision inspection system and to set tool properties in a second properties subset for each of the tools in the second tool subset, the second interface also usable to specify script expressions for the vision inspection system that cannot be specified using the first interface;

wherein, upon the selection of a first selected tool for one of the first and second selected sets of vision inspection tools, an instance of the first selected tool is added to a vision inspection system being specified;

wherein, upon the setting of a tool property for at least one tool included in one of the first and second tool subsets, a corresponding property of an associated vision inspection tool in the vision inspection system being specified is set;

wherein, the first interface and the second interface can be used to observe the first view and the second view of the vision inspection system, respectively, during the specifying of the vision inspection system;

wherein, the second view can be used to change the first tool subset and the first properties subsets, thereby changing the tools selectable and the properties settable via the first interface;

wherein, at least a subset of changes made to the vision inspection system using the first interface are represented as changes to the second interface in the second view; and wherein the first interface is a point-and-click interface and the second interface is a spreadsheet interface.

19. The system of claim 18 wherein inspection program expressions and values corresponding to inspection tools included in the second tool subset are presented in cells of the spreadsheet interface.

20. The system of claim 19 wherein the spreadsheet interface specifies cell set templates for at least a templated subset of the inspection tools included in the second tool subset where, when an inspection tool of the templated subset is selected using either one of the second interface and the first interface, an instance of a cell set template associated with the selected inspection tool is added to the second view included in the spreadsheet interface.

21. The system of claim 20 wherein at least a subset of the cell set templates include properties that may be accessed via the first interface and wherein the second interface can be used to render the properties exposed or hidden via the first interface.

22. The system of claim 18 wherein the second interface can be used to modify the first tool subset by at least one of adding a tool to the first tool subset and deleting a tool from the first tool subset.

23. The system of claim 18 wherein the second interface can be used to modify an existing tool and to store a new cell set template including cells that reflect modifications to the existing tool, where the new cell set template can be used subsequently to instantiate another tool instance having properties consistent with the modified existing tool.

24. The system of claim 18 wherein each change made to the vision inspection system using the first interface is reflected in the second view of the inspection system.

25. The system of claim 18 wherein the first tool subset includes a subset of the tools in the second tool subset.

26. The system of claim 18 wherein the second tool subset includes all of the tools available for specifying the vision inspection system.

27. The system of claim 18 wherein the first and second interfaces are presented via the display screen independent of each other.

28. The system of claim 18 wherein the first and second interfaces are presented via the display screen at different times.

29. A method for specifying vision inspection tools for a vision inspection system, the method comprising the steps of:

providing a first interface including a first view of the vision inspection system as the inspection system is being specified, the first interface usable to at least one of select, from a first tool subset, a first selected set of vision inspection tools to be used in the vision inspection system, and set tool properties in a first properties subset for each of the tools in the first tool subset; and providing a second interface including a second view of the vision inspection system as the inspection system is being specified, the second interface usable to at least one of select, from a second tool subset, a second selected set of vision inspection tools to be used with the vision inspection system and set tool properties in a second properties subset for each of a plurality of vision inspection tools, the second interface also usable to specify script expressions for the vision inspection system that cannot be specified using the first interface;

wherein, upon the selection of a first selected tool for one of the first and second selected sets of vision inspection tools using, respectively, one of the first and second interfaces, an instance of the first selected tool is added to the vision inspection system being specified;

wherein, upon the setting of a tool property for at least one tool included in one of the first and second tool subset using, respectively, one of the first and second interfaces, a corresponding property of an associated vision inspection tool in the vision inspection system being specified is set; and allowing the second interface and the first interface to be used to observe the second view and the first view of the vision inspection system, respectively, during the specifying of the vision inspection system;

wherein at least a first subset of changes made to the vision inspection system using the first interface are represented as changes to the second interface and at least a second subset of changes made to the vision inspection system using the second interface are represented as changes to the first interface, the first subset of changes including, at least in part, one of the selection of the first selected set of vision inspection tools and the setting of tool properties in the first properties subset, the second subset of changes including, at least in part, one of the selection of the second selected set of vision inspection tools and the setting of tool properties in the second properties subset; and wherein the first interface is a point-and-click interface and the second interface is a spreadsheet interface.

30. The system of claim 29 wherein the first and second interfaces are presented via the display screen independent of each other.

31. The system of claim 29 wherein the first and second interfaces are presented via the display screen at different times.

32. A method for specifying vision inspection tools for a vision inspection system, the method comprising the steps of:

providing a first interface including a first view of the vision inspection system as the inspection system is being specified, the first interface usable to select, from a first tool subset, a first selected set of vision inspection tools to be used in the vision inspection system and to set tool properties in a first properties subset for each of the tools in the first tool subset; and providing a second interface including a second view of the vision inspection system as the inspection system is being specified, the second interface usable to select, from a second tool subset, a second selected set of vision inspection tools to be used with the vision inspection system and to set tool properties in a second properties subset for each of the tools in the second tool subset, the second interface also usable to specify script expressions for the vision inspection system that cannot be specified using the first interface; and allowing the first interface and the second interface to be used to observe the first view and the second view of the vision inspection system, respectively, during the specifying of the vision inspection system;

wherein, upon the selection of a first selected tool for one of the first and second selected sets of vision inspection tools, an instance of the first selected tool is added to the vision inspection system being specified and, upon the setting of a tool property for at least one tool included in one of the first and second tool subsets, the property of an associated vision inspection tool in the vision inspection system being specified is set;

wherein, the second interface can be used to change the first tool subset and the first properties subsets, thereby changing the tools selectable and the properties settable via the first interface, respectively;

wherein, at least a subset of changes made to the vision inspection system using the first interface are represented as changes to the second interface; and wherein the first interface is a point-and-click interface and the second interface is a spreadsheet interface.

33. The system of claim 32 wherein the first and second interfaces are presented via the display screen independent of each other.

34. The system of claim 32 wherein the first and second interfaces are presented via the display screen at different times.

* * * * *